US008932627B2

(12) United States Patent
Barenholz et al.

(10) Patent No.: US 8,932,627 B2
(45) Date of Patent: Jan. 13, 2015

(54) LIPOSOMAL COMPOSITIONS OF GLUCOCORTICOID AND GLUCOCORTICOID DERIVATIVES

(75) Inventors: Yechezkel Barenholz, Jerusalem (IL); Alberto A. Gabizon, Jerusalem (IL); Yuval Avnir, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1700 days.

(21) Appl. No.: 11/662,172

(22) PCT Filed: Sep. 11, 2005

(86) PCT No.: PCT/IL2005/000963
§ 371 (c)(1),
(2), (4) Date: Oct. 5, 2007

(87) PCT Pub. No.: WO2006/027787
PCT Pub. Date: Mar. 16, 2006

(65) Prior Publication Data
US 2008/0058294 A1    Mar. 6, 2008

Related U.S. Application Data

(60) Provisional application No. 60/608,140, filed on Sep. 9, 2004.

(51) Int. Cl.
*A61K 9/127* (2006.01)
*A61K 31/573* (2006.01)

(52) U.S. Cl.
CPC ............. *A61K 9/1271* (2013.01); *A61K 31/573* (2013.01)
USPC ........................................................ 424/450

(58) Field of Classification Search
CPC .................................................... A61K 9/1271
USPC .......................................................... 424/450
See application file for complete search history.

(56) References Cited

U.S. PATENT DOCUMENTS 4,757,056 A * 7/1988 Van Gorp et al. ............... 514/54
5,013,556 A   5/1991 Woodle et al.
(Continued)

FOREIGN PATENT DOCUMENTS

DE   196 07 722 A1   9/1997
DE   102 55 106 A1   6/2004
(Continued)

OTHER PUBLICATIONS

Schmidt et al in Brain, vol. 126, pp. 1895-1904, 2003.*
(Continued)

*Primary Examiner* — Gollamudi Kishore
(74) *Attorney, Agent, or Firm* — Vorys, Sater, Seymour and Pease LLP; Susanne M. Hopkins; Ari G. Zytcer

(57) ABSTRACT

The present invention provides pharmaceutical compositions comprising a glucocorticoid or glucocorticoid derivative stably encapsulated in a liposome. The glucocorticoid or glucocorticoid derivative is selected from an amphipathic weak base glucocorticoid or glucocorticoid derivative having a pKa equal or below 11 and a logD at pH 7 in the range between −2.5 and 1.5; or an amphipathic weak acid GC or GC derivative having a pKa above 3.5 and a logD at pH 7 in the range between −2.5 and 1.5. The therapeutic effect of the pharmaceutical composition of the invention was exhibited in vivo with appropriate models of multiple sclerosis and cancer.

11 Claims, 7 Drawing Sheets

(56) References Cited

U.S. PATENT DOCUMENTS

| | | | |
|---|---|---|---|
| 5,189,018 A * | 2/1993 | Goldman et al. | 514/10.8 |
| 5,192,549 A | 3/1993 | Barenolz et al. | |
| 5,316,771 A | 5/1994 | Barenholz et al. | |
| 5,356,633 A * | 10/1994 | Woodle et al. | 424/450 |
| 5,395,619 A | 3/1995 | Zalipsky et al. | |
| 5,817,856 A | 10/1998 | Tirosh et al. | |
| 5,939,096 A | 8/1999 | Clerc et al. | |
| 6,043,094 A | 3/2000 | Martin et al. | |
| 6,090,800 A | 7/2000 | Unger et al. | |
| 6,165,501 A | 12/2000 | Tirosh et al. | |
| 6,313,179 B1 * | 11/2001 | Pope et al. | 514/724 |
| 7,048,943 B2 | 5/2006 | Barenholz et al. | |
| 2003/0059471 A1 * | 3/2003 | Compton et al. | 424/489 |
| 2003/0073619 A1 * | 4/2003 | Mahato et al. | 514/8 |
| 2003/0129222 A1 * | 7/2003 | Lopez-Berestein et al. | 424/450 |
| 2003/0185826 A1 * | 10/2003 | Tobinick | 424/145.1 |
| 2004/0219201 A1 | 11/2004 | Barenholz et al. | |
| 2005/0202078 A1 * | 9/2005 | Schiffelers et al. | 424/450 |
| 2006/0025446 A1 | 2/2006 | Sterling et al. | |
| 2006/0093595 A1 * | 5/2006 | Jayachandra | 424/94.2 |
| 2006/0147511 A1 * | 7/2006 | Panzner et al. | 424/450 |
| 2006/0148770 A1 * | 7/2006 | Fong et al. | 514/171 |
| 2010/0129437 A1 * | 5/2010 | Gaillard | 424/450 |

FOREIGN PATENT DOCUMENTS

| | | |
|---|---|---|
| JP | 56-161317 A | 12/1981 |
| WO | 90/06775 A1 | 6/1990 |
| WO | 98/07409 A1 | 2/1998 |
| WO | 02/45688 * | 6/2002 |
| WO | 02/45688 A2 | 6/2002 |
| WO | 03/005805 A1 | 1/2003 |
| WO | 03/032947 A2 | 4/2003 |
| WO | 03/053442 A1 | 7/2003 |
| WO | 2004/019916 A1 | 3/2004 |
| WO | 2004/047792 A2 | 6/2004 |

OTHER PUBLICATIONS

J. E. Trosko, Mutation Research 480-481, pp. 219-229, 2001.*

Trosko, et al., "Mechanism of up-regulated gap junctional intercellular communication during chemoprevention and chemotherapy of cancer", Mutation Research, vol. 480-481, pp. 219-229, (2001).

Uster, et al., "Insertion of poly(ethylene glycol) derivatized phospholipid into pre-formed liposomes results in prolonged in vivo circulation time", FEBS Letters, vol. 386, pp. 243-246, (1996).

Voisin, et al., "Extrapolation of Animal Toxicity to Humans: Interspecies Comparisons in Drug Development", Regulatory Toxicology and Pharmacology, vol. 12, pp. 107-116, (1990).

Weinberg, et al., "Prevention of catecholaminergic oxidative toxicity by 4-hydroxy-2,2,6,6-tetramethylpiperidine-1-oxyl and its recycling complex with polynitroxylated albumin, TEMPOL/PNA", Brain Research, vol. 1012, pp. 13-21, (2004).

Xia, et al., "Effect of glucocorticoid on cell cycle of human ovarian cancer cell line EO-8910", Acad J Sec Mil Med Univ, vol. 24, No. 5, pp. 499-501, (2003). Summary/Abstract in English—Article in Japanese.

Zuidam, et al., "Electrostatic and structural properties of complexes involving plasmid DNA and cationic lipids commonly used for gene delivery", Biochemica et Biophysica Acta, vol. 1368, pp. 115-128, (1998).

Abu Raya, et al., "A tissue culture ischemic device to study eicosanoid release by pheochromocytoma PC12 cultures", Journal of Neuroscience Methods, vol. 50, pp. 197-203, (1993).

Abu-Raya, et al., "Rasagiline, a Monoamine Oxidase-B Inhibitor, Protects NGF-Differentiated PC12 Cells Against Oxygen-Glucose Deprivation", Journal of Neuroscience Research, vol. 58, pp. 456-463, (1999).

Almawi, et al., "Molecular mechanisms of glucocorticoid antiproliferative effects: antagonism of transcription factor activity by glucocorticoid receptor", J. Leukoc. Biol., vol. 71, pp. 9-15, (2002).

Amselem, et al., "Preparation and Characterization of Liposomal Doxorubicin for Human Use", Journal of Liposome Research, vol. 2, No. 1, pp. 93-123, (1992).

Anderson, et al., "Initial Rate Studies of Hydrolysis and Acyl Migration in Methylprednisolone 21-Hemisuccinate and 17-Hemisuccinate", Journal of Pharmaceutical Sciences, vol. 70, No. 2, pp. 181-186, (1981).

Barenholz, et al., Liposome Technology 2nd Edition, vol. I, Liposome Preparation and Related Techniques, pp. 527-616, (1993).

Notice of References Cited, Part of Paper 20100215, for U.S. Appl. No. 11/662,174, three pages, (2010).

Coleman, "Glucocorticoids in cancer therapy", Biotherapy, vol. 4, pp. 37-44, (1992).

Cramer, et al., "NMR Studies of pH-Induced Transport of Carboxylic Acids Across Phospholipid Vesicle Membranes", Biochemical and Biophysical Research Communications, vol. 75, No. 2, (1977).

Deamer, et al., "The Response of Fluorescent Amines to pH Gradients Across Liposome Membranes", Biochemica et Biophysica Acta, vol. 274, pp. 323-335, (1972).

Ebadi, et al., "Oxidative Stress and Antioxidant Therapy in Parkinson's Disease", Progress in Neurobiology, vol. 48, pp. 1-19, (1996).

Ferrante, et al., "Evidence of Increased Oxidative Damage in Both Sporadic and Familial Amyotrophic Lateral Sclerosis", Journal of Neurochemistry, vol. 69, pp. 2064-2074, (1997).

Fildes, et al., "Interaction of cortisol-21-palmitate with liposomes examined by differential scanning calorimetry", Journal of Pharmacy and Pharmacology, vol. 30, No. 65, pp. 337-342, (1978). Abstract Only.

Folkman, et al., "Angiogenesis Inhibition and Tumor Regression Caused by Heparin or a Heparin Fragment in the Presence of Cortisone", Science, vol. 221, pp. 719-725, (1983).

Fuchs, et al., "Electron Paramagnetic Resonance Studies on Nitroxide Radical 2,2,5,5-Tetramethyl-4-Piperidin-1-Oxyl (Tempo) Redox Reactions in Human Skin", Free Radical Biology & Medicine, vol. 22, No. 6, pp. 967-976, (1997).

Garbuzenko, et al., "Electrostatics of PEGylated Micelles and Liposomes Containing Charged and Neutral Lipopolymers", Langmuir, vol. 21, pp. 2560-2568, (2005).

Gariboldi, et al., "Antiproliferative Effect of the Piperidine Nitroxide Tempol on Neoplastic and Nonneoplastic Mammalian Cell Lines", Free Radical Biology & Medicine, vol. 24, No. 6, pp. 913-923, (1998).

Gonzalez-Rothi, et al., "Pulmonary Targeting of Liposomal Triamcinolone Acetonide Phosphate", Pharmaceutical Research, vol. 13, No. 11, pp. 1966-1703, (1996).

Halliwell, "Role of Free Radicals in the Neurodegenerative Diseases", Drugs & Aging, vol. 18, No. 9, pp. 685-716, (2001).

Haran, et al., "Transmembrane ammonium sulfate gradients in liposomes produce efficient and stable entrapment of amphipathic weak bases", Biochemica et Biophysica Acta, vol. 1151, pp. 201-215, (1993).

Ilhan, et al., "Protective Effects of Caffeic Acid Phenethyl Ester Against Experimental Allergic Encephalomyelitis-Induced Oxidative Stress in Rats", Free Radical Biology & Medicine, vol. 37, No. 3, pp. 386-394, (2004).

Kedar, et al., "Delivery of Cytokines by Liposomes. I. Preparation and Characterization of Interleukin-2 Encapsulated in Long-Circulating Sterically Stabilized Liposomes", Journal of Immunotherapy, vol. 16, pp. 47-59, (1994).

Kohen, et al., "Reducing equivalents in the aging process", Archives of Gerontology and Geriatrics, vol. 24, pp. 103-123, (1997).

Lasic, et al., "Gelation of liposome interior: A novel method for drug encapsulation", FEBS, vol. 312, No. 2,3, pp. 255-258, (1992).

Lasic, et al., "Transmembrane gradient driven phase transitions within vesicles: lessons for drug delivery", Biochemica et Biophysica Acta, vol. 1239, pp. 145-156, (1995).

Lopez-Garcia, et al., "Intra-articular therapy of experimental arthritis with a derivative of triamcinolone acetonide incorporated in liposomes.", J Pharm Pharmacol., vol. 45, No. 6, pp. 576-578, (1993). Abstract Only.

(56) References Cited

OTHER PUBLICATIONS

Love, et al., "Specific accumulation of cholesterol-rich liposomes in the inflammatory tissue of rats with adjuvant arthritis", Annuals of the Rheumatic Diseases, vol. 49, pp. 611-614, (1990).

Lu, et al., "Oxidative damage to mitochondrial DNA and activity of mitochondrial enzymes in chronic active lesions of multiple sclerosis", Journal of the Neurological Sciences, vol. 177, pp. 95-103, (2000).

Lucchinetti, et al., "Heterogeneity of Multiple Sclerosis Lesions: Implications for the Pathogenesis of Demyelination", Ann Neurol, vol. 47, pp. 707-717, (2000).

Markesbery, et al., "Symposium: Oxidative Stress in Neurological Disease: Oxidative Alterations in Alzheimer's Disease", Brain Pathology, vol. 9, pp. 133-146, (1999).

Maruyama, "PEG-liposome in DDS and Clinical Studies", Nihon Rinsho, vol. 56, No. 3, pp. 632-637, (1998). Summary/Abstract in English—Article in Japanese.

Metselaar, et al., "Liposomal targeting of glucocorticoids to synovial lining cells strongly increases therapeutic benefit in collagen type II arthritis", Ann Rheum Dis, vol. 63, pp. 348-353, (2004).

Metselaar, et al., "Long-circulating liposomes for i.v. targeted delivery of glucocorticoids in arthritis.", Cell Mol Biol Lett, vol. 7, No. 2, pp. 291-292, (2002).

Metselaar, et al., "Complete Remission of Experimental Arthritis by Joint Targeting of Glucocorticoids With Long-Circulating Liposomes", Arthritis & Rheumatism, vol. 48, pp. 2059-2066, (2003).

Metselaar, et al., "Chapter 7: Therapeutic Index of Glucocorticoids can be Optimized by Encapsulating High-Clearance Glucocorticoids in Long-Circulating Liposomes", Liposomal targeting of glucocorticoids. A novel treatment approach for inflammatory disorders, pp. 107-122, (2003), Ph.D. Thesis,Utrecht University, Faculty of Pharmaceutical Sciences, Faculty of Veterinary Medicine ISBN 90-393-3285-1, available online: igitur-archive.library.uu.nl/dissertations/2006-0126-200506/c7.pdf.

Mishina, et al., "Liposomal methylprednisolone in rats: dose-proportionality and chronic-dose pharmacokinetics/pharmacodynamics.", Pharm Res., vol. 13, No. 1, pp. 141-145, (1996).

Mordenti, "Dosage Regimen Design for Pharmaceutical Studies Conducted in Animals", Journal of Pharmaceutical Sciences, vol. 75, No. 9, pp. 852-857, (1986).

Nichols, et al., "Catecholamine Uptake and Concentration by Liposomes Maintaining pH Gradients", Biochemica et Biophysica Acta, vol. 455, pp. 269-271, (1976).

Offen, et al., "Mice Overexpressing Bcl-2 in Their Neurons Are Resistant to Myelin Oligodendrocyte Glycoprotein (MOG)-Induced Experimental Autoimmune Encephalomyelitis (EAE)", Journal of Molecular Neuroscience, vol. 15, pp. 167-175, (2001).

Olsson, et al., "Forelimb Akinesia in the Rat Parkinson Model: Differential Effects of Dopamine Agonists and Nigral Transplants as Assessed by a New Stepping Test", The Journal of Neuroscience, vol. 15, No. 5, pp. 3863-3875, (1995).

Padki, et al., "Liposome-mediated functional targeting of prednisolone", Indian J Med Res, vol. 84, pp. 83-88, (1986).

Pollak, et al., "The EAE-associated behavioral syndrome: I. Temporal correlation with inflammatory mediators", Journal of Neuroimmunology, vol. 137, pp. 94-99, (2003).

Samuni, et al., "Nitroxide Sod-Mimics: Modes of Action", Free Rad. Res. Commun., vols. 12-13, Pt 1, pp. 187-194, (1991).

Samuni, et al., "Stable Nitroxide Radicals Protect Lipid Acyl Chains from Radiation Damage", Free Radical Biology & Medicine, vol. 22, No. 7, pp. 1165-1174, (1997).

Sarsero, et al., "Upregulation of expression from the FRDA genomic locus for the therapy of Friedreich ataxia", The Journal of Gene Medicine, vol. 5, pp. 72-81, (2003).

Schmidt, et al., "Drug targeting by long-circulating liposomal glucocorticosteroids increases therapeutic efficacy in a model of multiple sclerosis", Brain, vol. 126, pp. 1895-1904, (2003).

Senmei, et al., "A study of the relationship between of the contents of glucocorticoid receptors in multiple sclerosis patients and the efficacy of steroid therapy", China Academic Journal Electronic Publishing House, pp. 282-283, (2001). Summary/Abstract in English—Article in Japanese.

Shacter, et al., "Oxidative stress interferes with cancer chemotherapy: inhibition of lymphoma cell apoptosis and phagocytosis", Blood, vol. 96, pp. 307-313, (2000).

Shmeeda, et al., [17] Enzymatic Assays for Quality Control and Pharmacokinetics of Liposome Formulations: Comparison with Nonenzymatic Conventional Methodologies, Methods in Enzymology, vol. 367, pp. 272-292, (2003).

Tirosh, et al., "Hydration of Polyethylene Glycol-Grafted Liposomes", Biophysical Journal, vol. 74, pp. 1371-1379, (1998).

\* cited by examiner

LIPOSOMAL COMPOSITIONS OF GLUCOCORTICOID AND GLUCOCORTICOID DERIVATIVES

CROSS-REFERENCE

This is a National Phase Application filed under 35 U.S.C. 371 of International Application No. PCT/IL2005/000963, filed Sep. 11, 2005, claiming the benefit under 35 USC 119(e) of U.S. Provisional Application No. 60/608,140, filed Sep. 9, 2004, the entire contents of each of which is hereby incorporated herein by reference in its entirety.

FIELD OF THE INVENTION

This invention relates in general to liposome technology, and specifically, to the use of this technology for the delivery within the body of glucocorticoids.

LIST OF PRIOR ART

The following is a list of prior art which is considered to be pertinent for describing the state of the art in the field of the invention.

Gonzalez-Rothi, Ricardo J et al. *Pharmaceutical Research* 13(11):1699-1703 (1996);

Schmidt J et al. *Brain* 126(8):1895-1904 (2003);

Fildes F J et al. *J Pharm. Pharmacol.* 30(6):337-42 (1978);

Mishina E V et al *Pharm Res* 13(1):141-5 (1996);

Gonzalez-Rothi, Ricardo J et al. *Pharmaceutical Research* 13(11):1699-1703 (1996);

Almawi W Y and Melemedjian O K, *J Leukoc Biol* 71:9-15 (2002);

Coleman R E *Biotherapy* 4:37-44 (1992);

Folkman J, et al. *Science* 221:719-725 (1983);

Swain S. M., Endocrine therapies of cancer In, *Cancer Chemotherapy and Biotherapy*, 2nd Ed., Eds., Chabner B A, and Longo D L, Lippincott-Raven, Philadelphia, 1996, (pp 59-108);

Haskell C M. In, Cancer Treatment, 4th Edition, Edited by Haskell C M, and Berek J S. WB Saunders Co, Philadelphia, 1995 (pp 78-80, pp 105-106, pp 151-152).

Josbert M. Metselaar, Liposomal targeting of glucocorticoids. A novel treatment approach for inflammatory disorders. Chapter 6, pp 91-106, chapter 7, pp 107-122, 2003, Ph.D. Thesis, Utrecht University, Faculty of Pharmaceutical Sciences, Faculty of Veterinary Medicine ISBN 90-393-3285-1;

BACKGROUND OF THE INVENTION

Glucocorticoids (glucocorticosteroids) are a class of steroid hormones characterized by an ability to bind with the cortisol receptor found in the cells of almost all vertebrate tissues and trigger similar effects. Glucocorticoids are distinguished from other steroids such as sex steroids by the specific receptors, target cells, and effects. Cortisol (or hydrocortisone) is the most important natural human glucocorticoid.

Glucocorticoids have potent anti-inflammatory and immunosuppressive properties. This is particularly evident when they are administered at pharmacologic doses, but also is important in physiologic immune responses. As a consequence, glucocorticoids are widely used as drugs to treat inflammatory conditions such as arthritis or dermatitis, and as adjunctive therapy for conditions such as autoimmune diseases. On the other hand, excessive glucocorticoid levels, resulting from administration as a drug or hyperadrenocorticism have side-effects on many systems, some examples including inhibition of bone formation, suppression of calcium absorption and delayed wound healing.

A variety of synthetic glucocorticoids, some far more potent than cortisol, have been developed for therapeutic use. They differ in the pharmacokinetics (absorption factor, half-life, volume of distribution, clearance) and in pharmacodynamics (for example the capacity of mineralocorticoid activity: retention of sodium ($Na^+$) and water). Because they are absorbed well through the intestines, they are primarily administered per os (by mouth), but also by other ways like topically on skin.

Methylprednisolone (pregna-1,4-diene-3,20-dione,11,17,21-trihydroxy-6-methyl-,(6α,11β). $C_{22}H_{30}O_5$, MW 374.48) is one example of a therapeutically potent synthetic glucocorticoid drug, which, due to its hydrophobic character, is usually taken orally. Like most adrenocortical steroids, methylprednisolone is typically used for its anti-inflammatory properties. However, glucocorticoids have a wide range of effects, including changes in metabolism and immune responses. Similar to other corticosteroids, the list of diseases or pathological conditions for which methlyprednisolone is effective is rather large. Common uses includes arthritis therapy, and short-term treatment of bronchial inflammation due to various respiratory diseases. while hightly effective, their systemic application is limited because of a high incidence of serious adverse effects, especially related to long-term treatment.

Efficacy and safety studies of systemic administration of glucocorticoids, revealed that in addition to the profound activity of the drug in many different tissues, these drugs have rapid clearance from plasma thereby requiring high and frequent dosing to obtain effective amounts at the target site.

Thus, alternative approaches for parenteral administration were investigated. For example, developing loco-regional administration of glucocorticoids (e.g. by the use of inhalers in asthma and in intraarticular injection in arthritis) enabled the use of lower doses of the steroid while achieving sufficient drug levels in a lesion, with minimal side effects.

A further approach included targeting of the drug to the target tissue by the use of a suitable carrier, such as liposomes.

First attempts to encapsulate corticosteroids in liposomes were performed by Fildes F J et al. [J Pharm. Pharmacol. 30(6):337-42 (1978)] which included steroid encapsulation in the liposome's lipid bilayer. This approach was based on the understanding that corticosteroids are hydrophobic in nature. However, such liposomal formulations turned to be unsuitable for clinical applications.

Efforts were also made in developing "soluble" glucocorticoids. Examples include succinate derivatized steroids such as hydrocortisone hemisuccinate sodium salt and Methylprednisolone hemisuccinate sodium salt. Another group of soluble glucocorticoids include the phosphate derivatives of steroids. While rendering the steroid water-soluble enabled the use of the acidic steroids for injection, it was shown that these "pro-drugs" are completely cleared from plasma in less than 6 hours post injection. [Mishina E V et al *Pharm Res* 13(1):141-5 (1996)]

The combination of acidic steroids with liposomes was also investigated. Schmidt et al. [Schmidt J et al. *Brain* 126 (8):1895-1904 (2003)] describe a formulation of polyethyleneglycol (PEG)-coated long-circulating sterically stabilized liposomes encapsulating prednisolone phosphate (one of the water soluble pro-drug steroids) and its beneficial effect in treating multiple sclerosis as compared to the free form of the steroid. However, attempts to similarly encapsulate methylprednisolone hemisuccinate (a weak acid) failed, as it led to an unstable formulation.

Further, encapsulation in liposomes of triamcinolone acetonide phosphate, a water soluble strong acid derivative of triamcinolone (pKa below 2) was described [Gonzalez-Rothi, Ricardo J et al. *Pharmaceutical Research* 13(11):1699-1703 (1996)]. The liposomal formulation was prepared by passive loading of the acidic corticosteroid into the liposomes and used as an injectable dosage form (intravenous or intratracheal) for treating pulmonary conditions. Further, in ex vivo stability studies it was shown that after 24 hours the liposome retained more than 75% of the acidic corticosteroid.

SUMMARY OF THE INVENTION

The invention is based on the finding that using chemically modified gluococorticoids (GC), in their amphipathic weak acid form enables the effective loading in liposomes of the acidic GC. Surprisingly, the thus formed liposomal weakly acidic GC was stable, i.e. the majority of the substance remained within the liposome as intact acidic GC after storage for 14 months at 4° C. Once released from the liposome to water or body fluids the acidic GC was hydrolyzed to obtain the active, non-acidic GC.

Thus, according to a first of its aspects the invention provides a pharmaceutical composition comprising a GC or GC derivative encapsulated in a liposome, wherein said GC or GC derivative is essentially retained in said liposome for 6 months, preferably 10 months and more preferably 14 months, the GC or GC derivative being selected from:
  i) an amphipathic weak base GC or GC derivative having a pKa equal or below 11 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

The GC derivative is preferably an acidic GC, i.e. an amphipathic weak acid derivative of GC which is converted to the non-acidic form upon release from the liposome to bodily fluids. More specifically, the acidic GC is methylprednisolone sodium hemisuccinate (MPS).

A preferred MPS formulation according to the invention comprises sterically stabilized liposomes formed from a combination of hydrogenated soybean phosphatidylcholine (HSPC), (methyl)polyethylene glycol coated distearoyl phosphatidyl ethanolamine (PEG-DSPE) and cholesterol at a molar ratio of 55:40:5.

The pharmaceutical composition is preferably utilized for the treatment or prevention of any disease whose acceptable form of treatment includes administration of glucocorticoids.

The pharmaceutical composition in accordance with the invention in generally better than the non-encapsulated GC in at least one of: better delivery to the target site, better circulation time, slower clearance, reduced side effect, increased efficacy or increased therapeutic index.

The pharmaceutical composition is preferably utilized for the treatment or prevention of multiple sclerosis.

The pharmaceutical composition is also preferably utilized for the treatment or prevention of cancer which are known to be sensitive to steroids, such as cancers of haematopoeitic origin including lymphoma, leukemia, myeloma, breast cancer and prostate cancer.

The invention also provides the use of GC or GC derivative for the preparation of the pharmaceutical composition of the invention, the GC or GC derivative being encapsulated in a liposome, wherein said GC or GC derivative is essentially retained in said liposome for 6 months, preferably 10 months and more preferably 14 months, the GC or GC derivative being selected from:
  i) an amphipathic weak base GC or GC derivative having a pKa equal or below 11 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

Yet further, the invention provides a method for delivery of a glucocorticoid (GC), preferably a water immiscible GC, to a target site within a body, comprising chemically modifying said GC to an amphipathic weak acid derivative or amphipathic weak based derivative thereof, and loading said amphipatlic weak acid derivative or amphipathic weak base derivative into a liposome. Specifically, the liposome is a sterically stabilized liposome and the GC derivative is loaded into the liposome by the formation of an ion or pH gradient across the liposome membrane (i.e. by active loading techniques).

Yet further, the invention provides a method of the treatment or prevention of a disease or pathological condition comprising administering to a subject in need an amount of GC or GC derivative encapsulated in liposomes, the amount being sufficient to achieve a therapeutic effect.

Preferably, the method comprises injection of the liposomes encapsulating GC or GC derivative.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
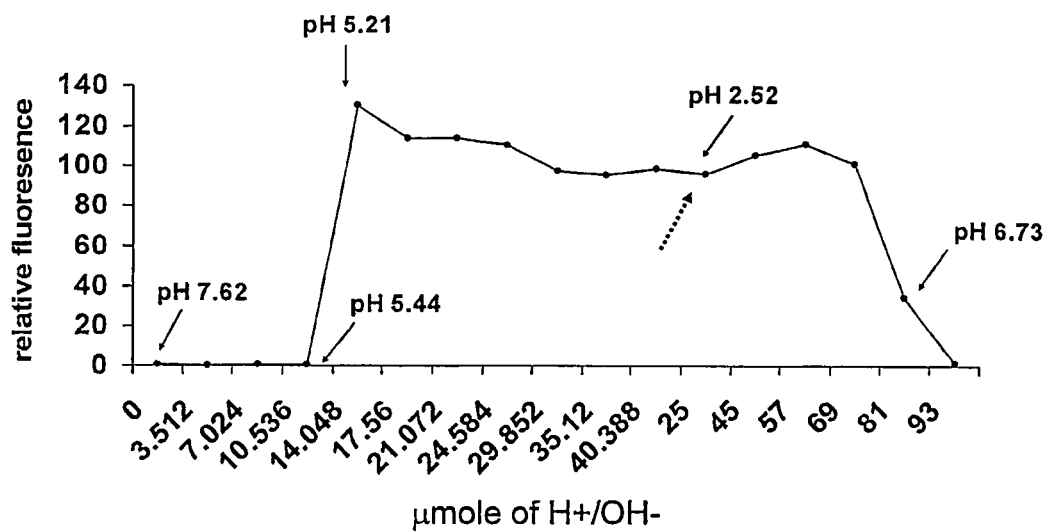
FIGS. 1A-1C are graphs showing chemical characteristics of methylprednisolone sodium hemisuccinate (MPS), including turbidity of MPS as function of pH (FIG. 1A); partition coefficient of MPS at different pH points (FIG. 1B); and surface tension of methylprednisolone hemisuccinate and dexamethasone phosphate as function of GC concentration (FIG. 1C).

Glucocorticoids (GCs) are a family of hormones that predominantly affects the metabolism of carbohydrates and, to a lesser extent, fats and proteins (and have other effects). Glucocorticoids are made in the peripheral part (the cortex) of the adrenal gland and chemically classed as steroids. Cortisol is the major natural glucocorticoid. Nonetheless, the term glucocorticoid also applies to equivalent hormones synthesized in the laboratory.

A non-limiting list of glucocorticoids may be found at the internet site http://www.steraloids.com/, incorporated herein in its entirety by reference. Examples include prednisolone hemisuccinate, methylprednisolone heeimisuccinate, dexamethasone hemisuccinate, allopregnanolone hemisuccinate; beclomethasone 21-hemisuccinate; betamethasone 21-hemisuccinate; boldenone hemisuccinate; prednisolone hemisuccinate, sodium salt; prednisolone 21-hemisuccinate; nandrolone hemisuccinate; 19-nortestosterone hemisuccinate; deoxycorticosterone 21-hemisuccinate; dexamethasone hemisuccinate; dexamethasone hemisuccinate spermine; corticosterone hemisuccinate; cortexolone hemisuccinate.

Like with many other medicaments, administration of GC in a free form may posses some disadvantages, such as the risk of exposing the treated individual to side effects known to occur with GC treatment, rapid clearance of the steroid from the plasma, etc.

In the search to overcome such disadvantages, the inventors have envisaged that while it is difficult to efficiently and stably load in a vehicle the rather hydrophobic GC, by applying a rather simple chemical modification on the glucocorticoid involving the conversion of the steroid to a water-soluble derivate, it is possible to load the derivate into liposomes.

Thus, the present invention provides stable pharmaceutical compositions comprising a glucocorticoid (GC) or GC derivative encapsulated in a liposome, wherein said GC or GC derivative is essentially retained in said liposome for 6, preferably 10, more preferably 14 months (when stored at 4° C.), the GC or GC derivative being selected from:
  i) an amphipathic weak base GC or GC derivative having a pKa equal or above 1 and a logD at pH 7 in the range between about −2.5 and about 1.5, preferably, in the range between about −1.5 and about 1.0;
  ii) an amphipathic weak acid GC or GC derivative having a pKa above 3.5 and a logD at pH 7 in the range between about −2.5 and about 1.5, preferably, in the range between about −1.5 and about 1.0.

The term "GC derivative" as used herein denotes a GC molecule which was chemically modified either by the insertion of a chemical group or by the removal of a chemical group from the GC molecule, the modification results in the conversion of the molecule to an amphipathic weak base or amphipathic weak acid, depending on the type of modification applied. As well appreciated by those versed in the chemistry of steroids, these hydrophilic in nature molecules posses at least one chemically reactive group which may be conjugated with a weak acid or weak base to form a respective amphipathic weak acid or amphipathic weak base molecule. Non-limiting examples of chemically reactive group typically included in the general structure of steroids are hydroxyl, carboxyl, and the like, as known to those versed in chemistry. It should be noted that in the context of the present invention GC derivative may also encompass an active, non-modified, amphipathic and weakly acid GC.

The GC derivative by one aspect is a pro-drug, i.e. it has no pharmacological activity in the form it is present in the liposome. Upon release from the liposome the GC pro-drug in converted by enzymes, such as esterases, to its pharmacologically active hydrophobic form.

In accordance with yet another aspect the GC encapsulated in the liposome, is already in its pharmaceutically active form, and does not have to undergo any enzymatic processing in order to become active. In accordance with the second aspect the GC itself is a weak amphipathic acid or base.

The term "amphipathic weak acid" is used herein to denote a molecule having both hydrophobic and hydrophilic groups, the steroid backbone of the GC essentially constituting the hydrophobic group, while the weak acid moiety linked to the GC by virtue of the modification described above essentially constituting the hydrophilic group. The GC amphipathic weak acid or GC derivative is characterized by the following physical characteristics:
  pKa: it has a pKa above 3.0, preferably above 3.5, more preferably, in the range between about 3.5 and about 6.5;
  Partition coefficient: in an n-octanol/buffer (aqueous phase) system having a pH of 7.0, it has a logD in the range between about −2.5 and about 1.5 and more preferably between about −1.5 and about 1.0.

Such amphipathic weak acid derivatives of GC may be obtained by reacting the GC with dicarbocylic or tricarboxylic acids or by linking the GC to the amino group of the amino acid, by techniques known to those versed in the art.

Specific examples of GC derivates include, without being limited thereto, betamethasone 21-hemisuccinate prednisolone hemisuccinate sodium salt; prednisolone 21-hemisuccinate; dexamethasone hemisuccinate; dexamethasone hemisuccinate:spermine; corticosterone hemisuccinate Prednisolone hemisuccinate; Methylprednisolone heeimisuccinate; Dexamethasone hemisuccinate.

The term "amphipathic weak base" is used herein to denote a molecule having both hydrophobic and hydrophilic groups, the steroid backbone of the GC essentially constituting the hydrophobic group, while the weak base moiety linked to the GC by virtue of the modification described above essentially constituting the hydrophilic group. The GC amphipathic weak acid derivative is characterized by the following physical characteristics:
  pKa: it has a pKa below 11.0, more preferably between about 11.0 and about 7.5;
  Partition coefficient: in an n-octanol/buffer (aqueous phase) system it has a logD in the range between about −2.5 and about 1.5 and more preferably between about −1.5 and about 1.0.

Such amphipathic weak base derivatives of GC may be obtained by reacting the GC with basic amino acids, such as arginine or lysine or with any amino acid through its carboxy group, leaving the amino group free or with polyamine such as spermidine or spermine.

The term "liposome" is used herein to denote lipid based bilayer vesicles. Liposomes are widely used as biocompatible carriers of drugs, peptides, proteins, plasmic DNA, antisense oligonucleotides or ribozymes, for pharmaceutical, cosmetic, and biochemical purposes. The enormous versatility in particle size and in the physical parameters of the lipids affords an attractive potential for constructing tailor-made vehicles for a wide range of applications. Different properties (size, colloidal behavior, phase transitions, electrical charge and polymorphism) of diverse lipid formulations (liposomes, lipoplexes, cubic phases, emulsions, micelles and solid lipid nanoparticles) for distinct applications (e.g. parenteral, transdermal, pulmonary, intranasal and oral administration) are available and known to those versed in the art. These properties influence relevant properties of the liposomes, such as liposome stability during storage and in serum, the bio-distribution and passive or active (specific) targeting of cargo, and how to trigger drug release and membrane disintegration and/or fusion.

The present invention is applicable for a variety of liposome compositions and those versed in the art will know how to select the constituents of the liposome depending on the various considerations including the choice of GC or GC derivative, the mode of administration of the final liposomal formulation and others.

The liposomes are those composed primarily of liposome-forming lipids which are amphiphilic molecules essentially characterized by a packing parameter 0.74-1.0, or by a lipid mixture having an additive packing parameter (the sum of the packing parameters of each component of the liposome times the mole fraction of each component) in the range between 0.74 and 1.

Liposome-forming lipids, exemplified herein by phospholipids, form into bilayer vesicles in water. The liposomes can also include other lipids incorporated into the lipid bilayers, such as phosphatidyl ethanolamine (PE) and sterol, with their hydrophobic moiety in contact with the interior, hydrophobic region of the bilayer membrane, and the head group moiety oriented toward the exterior, polar surface of the bilayer membrane. The type and level of the additional, non-liposome forming lipid components will be determined by the additive packing parameter of the entire components of the lipid bilayer to remain in the range of 0.74-1.0.

The liposome-forming lipids are preferably those having a glycerol backbone wherein at least one, preferably two, of the hydroxyl groups at the head group is substituted with, preferably an acyl chain (to form an acyl or diacyl derivative), however, may also be substituted with an alkyl or alkenyl chain, a phosphate group or a combination or derivatives of same and may contain a chemically reactive group, (such as an amine, acid, ester, aldehyde or alcohol) at the headgroup, thereby providing a polar head group. Sphyngolipids, such as sphyngomyelins, are good alternative to glycerophopholipids.

Typically, the substituting chain(s), e.g. the acyl, alkyl or alkenyl chain is between 14 to about 24 carbon atoms in length, and has varying degrees of saturation being fully, partially or non-hydrogenated lipids. Further, the lipid may be of natural source, semi-synthetic or fully synthetic lipid, and neutral, negatively or positively charged. There are a variety of synthetic vesicle-forming lipids and naturally-occurring vesicle-forming lipids, including the phospholipids, such as phosphatidylcholine (PC), phosphatidylinositol (PI), phosphatidylglycerol (PG), dimyristoyl phosphatidylglycerol (DMPG); egg yolk phosphatidylcholine (EPC), 1-palmitoyl-2-oleoylphosphatidyl choline (POPC), distearoylphosphatidylcholine (DSPC), dimyristoyl phosphatidylcholine (DMPC); phosphatidic acid (PA), phosphatidylserine (PS) 1-palmitoyl-2-oleoylphosphatidyl choline (POPC), and the sphingophospholipids such as sphingomyelins (SM) having 12-24 carbon atom acyl or alkyl chains. The above-described lipids and phospholipids whose hydrocarbon chain (acyl/alkyl/alkenyl chains) have varying degrees of saturation can be obtained commercially or prepared according to published methods. Other suitable lipids include in the liposomes are glyceroglycolipids and sphingoglycolipids and sterols (such as cholesterol or plant sterol).

Preferably, the phospholipid is egg phophatidylcholine (EPC), 1-palmitoyl-2-oleoylphosphatidyl choline (POPC), distearoylphosphatidylcholine (DSPC) or hydrogenated soy phosphatidylcholine (HSPC).

Cationic lipids (mono and polycationic) are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Monocationic lipids may include, for example, 1,2-dimyristoyl-3-trimethylammonium propane (DMTAP) 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethyl-ammonium bromide (DORIE); N-[1-(2,3-dioleyloxy)propyl]-N,N,N-trimethylammonium chloride (DOTMA); 3β[N—(N',N'-dimethylaminoethane)carbamoly]cholesterol (DC-Chol); and dimethyl-dioctadecylammonium (DDAB).

Examples of polycationic lipids include a similar lipophilic moiety as with the mono cationic lipids, to which polycationic moiety is attached. Exemplary polycationic moieties include spermine or spermidine (as exemplified by DOSPA and DOSPER), or a peptide, such as polylysine or other polyamine lipids. For example, the neutral lipid (DOPE) can be derivatized with polylysine to form a cationic lipid. polycationic lipids include, without being limited thereto, N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS).

The lipids mixture forming the liposome can be selected to achieve a specified degree of fluidity or rigidity, to control the stability of the liposome in serum and to control the rate of release of the entrapped agent in the liposome.

Further, the liposomes may also include a lipid derivatized with a hydrophilic polymer to form new entities known by the term lipopolymers. Lipopolymers preferably comprise lipids modified at their head group with a polymer having a molecular weight equal or above 750 Da. The head group may be polar or apolar, however, is preferably a polar head group to which a large (>750 Da) highly hydrated (at least 60 molecules of water per head group) flexible polymer is attached. The attachment of the hydrophilic polymer head group to the lipid region may be a covalent or non-covalent attachment, however, is preferably via the formation of a covalent bond (optionally via a linker). The outermost surface coating of hydrophilic polymer chains is effective to provide a liposome with a long blood circulation lifetime in vivo. The lipopolymer may be introduced into the liposome by two different ways: (a) either by adding the lipopolymer to a lipid mixture forming the liposome. The lipopolymer will be incorporated and exposed at the inner and outer leaflets of the liposome bilayer [Uster P. S. et al. FEBBS Letters 386:243 (1996)]; (b) or by firstly prepare the liposome and then incorporate the lipopolymers to the external leaflet of the pre-formed liposome either by incubation at temperature above the Tm of the lipopolymer and liposome-forming lipids, or by short term exposure to microwave irradiation.

Preparation of vesicles composed of liposome-forming lipids and derivatization of such lipids with hydrophilic polymers (thereby forming lipopolymers) has been described, for example by Tirosh et al. [Tirosh et al., Biopys. J., 74(3):1371-1379, (1998)] and in U.S. Pat. Nos. 5,013,556; 5,395,619; 5,817,856; 6,043,094, 6,165,501, incorporated herein by reference and in WO 98/07409. The lipopolymers may be non-ionic lipopolymers (also referred to at times as neutral lipopolymers or uncharged lipopolymers) or lipopolymers having a net negative or a net positive charge.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers.

While the lipids derivatized into lipopolymers may be neutral, negatively charged, as well as positively charged, i.e. there is no restriction to a specific (or no) charge, the most commonly used and commercially available lipids derivatized into lipopolymers are those based on phosphatidyl ethanolamine (PE), usually, distearylphosphatidylethanolamine (DSPE).

A specific family of lipopolymers employed by the invention include monomethylolated PEG attached to DSPE (with different lengths of PEG chains, the methylated PEG referred to herein by the abbreviation PEG) in which the PEG polymer is linked to the lipid via a carbamate linkage resulting in a negatively charged lipopolymer. Other lipopolymer are the neutral methyl polyethyleneglycol distearoylglycerol (mPEG-DSG) and the neutral methyl polyethyleneglycol oxycarbonyl-3-amino-1,2-propanediol distearoylester (mPEG-DS) [Garbuzenko O. et al., Langmuir. 21:2560-2568 (2005)]. The PEG moiety preferably has a molecular weight of the head group is from about 750 Da to about 20,000 Da. More preferably, the molecular weight is from about 750 Da to about 12,000 Da and most preferably between about 1,000 Da to about 5,000 Da. One specific PEG-DSPE employed herein is that wherein PEG has a molecular weight of 2000 Da, designated herein $^{2000}$PEG-DSPE or $^{2k}$PEG-DSPE.

Preparation of liposomes including such derivatized lipids has also been described, where typically, between 1-20 mole percent of such a derivatized lipid is included in the liposome formulation.

It is well established that preparation of liposomal formulation involve the selection of an appropriate lipid composition in addition to the aqueous phase ingredients, such as buffers, antioxidants, metal chelators, and cryoprotectants. Charge-inducing lipids, such as phosphatidylglycerol can be incorporated into the liposome bilayer to decrease vesicle-vesicle fusion, and to increase interaction with cells, while cholesterol and sphingomyelin can be included in formulations in order to decrease permeability and leakage of encapsulated drugs. Buffers at neutral pH can decrease hydrolysis. Addition of an antioxidant, such as sodium ascorbate can decrease oxidation, etc.

Variations in ratios between these liposome constituents, dictates the pharmacological properties of the liposome, including stability of the liposomes, which is a major concern for various types of vesicular applications. Evidently, the stability of liposomes should meet the same standards as conventional pharmaceuticals. Chemical stability involves prevention of both the hydrolysis of ester bonds in the phospholipid bilayer and the oxidation of unsaturated sites in the lipid chain. Chemical instability can lead to physical instability or leakage of encapsulated drug from the bilayer and fusion and aggregation of vesicles. Chemical instability also results in short blood circulation time of the liposome, which affects the effective access to and interaction with the target.

A preferred formulation according to the invention is that comprising phosphatidylcholine (PC) such as egg PC (EPC) or hydrogenated soy PC (HSPC) as a the liposome forming lipid, PEGylated (2000 Da) distearoyl-phosphatidylethanolamine (PEG-DSPE) and cholesterol. Evidently, other lipids mixtures may be utilized in the same, similar or different mole ratio, and provided that the final additive packing parameter of the different constituents of the liposome is in the range of between about 0.74 and 1.0.

Figure 3A:
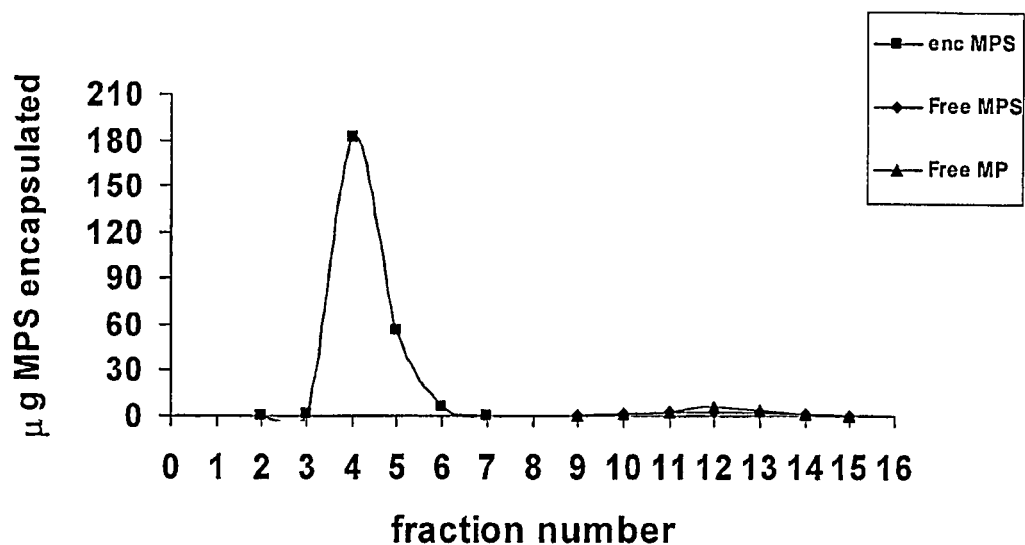
FIG. 3A-3B are size exclusion chromatography of SSL-MPS after 14 months of storage at 4° C. with FIG. 3B being an enlargment of the section describing fractions 8-17 of FIG. 3A showing existance of very low amounts of free MPS and methylprednisolone (MP).
Figure 3B:
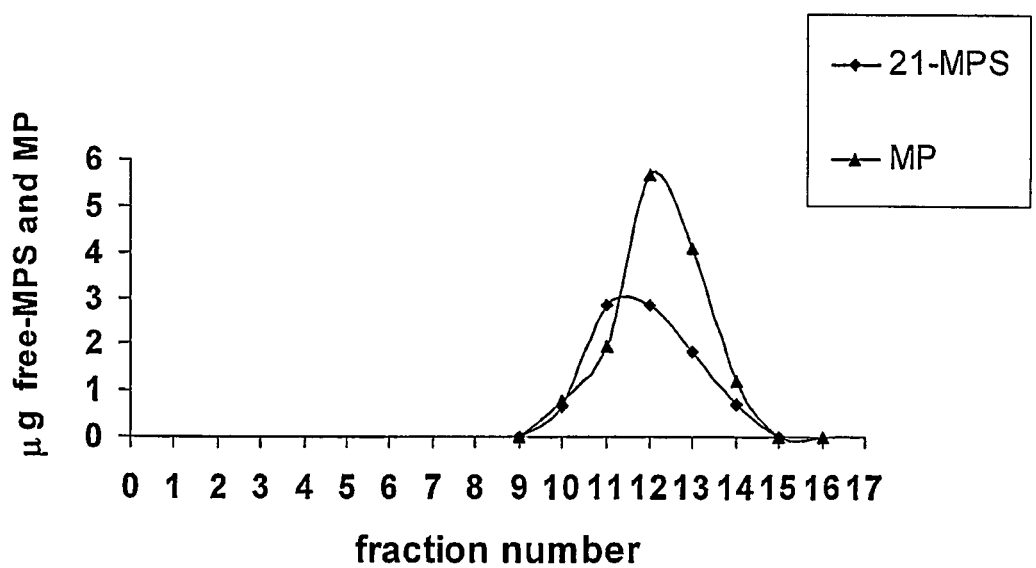

The pharmaceutical formulation of the invention was proven to be highly stable. An exemplified embodiment of the invention in which the GC derivative, Methylprednisolone succinate (methylprednisolone modified with succinic acid) was encapsulated in a liposome comprising the above three constituents, was shown to have only marginal reduction (less than 20% from initial concentration) in the GC derivative after storage at 4° C. for 14 months (FIGS. 3A-3B).

Thus, in the context of the present invention, the term "stability" denotes a formulation which under conventional storage conditions (4° C.) retains the majority (more than 80%, preferably more than 90%) of the GC/GC derivative in the liposome, for 6 months, preferably for 10 months and more preferably for 14 months. Accordingly, the term "essentially retains" used herein denotes that 80% and preferably 90% of the GC or GC derivative is retained in the liposomes under storage conditions for about 6, preferably 10 and more preferably 14 months. According to one preferred embodiment, stability of the liposomes is maintained by the use of sterically stabilized liposome (SSL), i.e. liposomes coated with a hydrophilic component. According to a preferred embodiment, the SSL comprises a combination of hydrogenated soy phosphatidylcholine (HSPC), $^{2000}$PEG-DSPE and cholesterol at a molar ratio of 55:40:5.

In general, there are a variety of drug-loading methods available for preparing liposomes with entrapped drug, including passive entrapment and active remote loading. The passive entrapment method is most suited for entrapping of lipophilic drugs in the liposome membrane and for entrapping drugs having high water solubility. In the case of ionizable hydrophilic or amphipathic drugs, even greater drug-loading efficiency can be achieved by loading the drug into liposomes against a transmembrane ion gradient [Nichols, J. W., et al., Biochim. Biophys. Acta 455:269-271 (1976); Cramer, J., et al., Biochemical and Biophysical Research Communications 75(2):295-301 (1977)]. This loading method, generally referred to as remote loading, typically involves a drug which is amphipathic in nature and has an ionizable group which is loaded by adding it to a suspension of liposomes having a higher inside/lower outside H$^+$ and/or ion gradient.

The liposomes employed in the context of the present invention are preferably loaded by the remote loading principle. The resulting formulation exhibited a significantly high GC derivative to lipid ratio. Preferably, the mole ratio between the GC derivative and lipid is between 0.01 and 2.0, more preferably, between 0.04 and 0.25. For high loading of the GC derivative it is at times preferable that the concentration of the same in the liposome be such that it precipitates in the presence of a pre-entrapped counter ion.

Liposomes having an H$^+$ and/or ion gradient across the liposome bilayer for use in remote loading can be prepared by a variety of techniques. A typical procedure comprises dissolving a mixture of lipids at a ratio that forms stable liposomes in a suitable organic solvent and evaporated in a vessel to form a thin lipid film. The film is then covered with an aqueous medium containing the solute species that will form the aqueous phase in the liposome interior space. After liposome formation, the vesicles may be sized to achieve a size distribution of liposomes within a selected range, according to known methods. The liposomes utilized in the present invention are preferably uniformly sized to a selected size range between 70-100 nm, preferably about 80 nm.

After sizing, the external medium of the liposomes is treated to produce an ion gradient across the liposome membrane (typically with the same buffer used to form the liposomes), which is typically a higher inside/lower outside ion concentration gradient. This may be done in a variety of ways, e.g., by (i) diluting the external medium, (ii) dialysis against the desired final medium, (iii) gel exclusion chromatography, e.g., using Sephadex G-50, equilibrated in the desired medium which is used for elution, or (iv) repeated high-speed centrifugation and resuspension of pelleted liposomes in the desired final medium. The external medium which is selected will depend on the type of gradient, on the mechanism of gradient formation and the external solute and pH desired, as will now be described.

In the simplest approach for generating an ion and/or $H^+$ gradient, the lipids are hydrated and sized in a medium having a selected internal-medium pH. The suspension of the liposomes is titrated until the external liposome mixture reaches the desired final pH, or treated as above to exchange the external phase buffer with one having the desired external pH. For example, the original hydration medium may have a pH of 5.5, in a selected buffer, e.g., glutamate, citrate, succinate, fumarate buffer, and the final external medium may have a pH of 8.5 in the same or different buffer. The common characteristic of these buffers is that they are formed from acids which are essentially liposome impermeable. The internal and external media are preferably selected to contain about the same osmolarity, e.g., by suitable adjustment of the concentration of buffer, salt, or low molecular weight non-electrolyte solute, such as dextrose or sucrose.

In another general approach, the gradient is produced by including in the liposomes, a selected ionophore. To illustrate, liposomes prepared to contain valinomycin in the liposome bilayer are prepared in a potassium buffer, sized, then the external medium exchanged with a sodium buffer, creating a potassium inside/sodium outside gradient. Movement of potassium ions in an inside-to-outside direction in turn generates a lower inside/higher outside pH gradient, presumably due to movement of protons into the liposomes in response to the net electronegative charge across the liposome membranes [Deamer, D. W., et al., Biochim. et Biophys. Acta 274:323 (1972)].

A similar approach is to hydrate the lipid and to size the formed multilamellar liposome in high concentration of magnesium sulfate. The magnesium sulfate gradient is created by dialysis against 20 mM HEPPES buffer, pH 7.4 in sucrose. Then, the A23187 ionophore is added, resulting in outwards transport of the magnesium ion in exchange for two protons for each magnesium ion, plus establishing a inner liposome high/outer liposome low proton gradient [Senske D B et al. (Biochim. Biophys. Acta 1414: 188-204 (1998)].

In another more preferred approach, the proton gradient used for drug loading is produced by creating an ammonium ion gradient across the liposome membrane, as described, for example, in U.S. Pat. Nos. 5,192,549 and 5,316,771, incorporated herein by reference. The liposomes are prepared in an aqueous buffer containing an ammonium salt, such as ammonium sulfate, ammonium phosphate, ammonium citrate, etc., typically 0.1 to 0.3 M ammonium salt, at a suitable pH, e.g., 5.5 to 7.5. The gradient can also be produced by including in the hydration medium sulfated polymers, such as dextran sulfate ammonium salt, heparin sulfate ammonium salt or sucralfate. After liposome formation and sizing, the external medium is exchanged for one lacking ammonium ions. In this approach, during the loading the amphipathic weak base is exchanged with the ammonium ion.

Yet, another approach is described in U.S. Pat. No. 5,939,096, incorporated herein by reference. In brief, the method employs a proton shuttle mechanism involving the salt of a weak acid, such as acetic acid, of which the protonated form trans-locates across the liposome membrane to generate a higher inside/lower outside pH gradient. An amphipathic weak acid compound is then added to the medium to the pre-formed liposomes. This amphipathic weak acid accumulates in liposomes in response to this gradient, and may be retained in the liposomes by cation (i.e. calcium ions)-promoted precipitation or low permeability across the liposome membrane, namely, the amphipathic weak acid is exchanges with the acetic acid.

The liposomes loaded with the GC or GC derivative may be administered in various ways. It may be formulated in combination with physiologically acceptable excipients, as known in the art. The pharmaceutically acceptable excipients employed according to the invention generally include inert, non-toxic substances which preferably do not react with liposomes. The excipients may be any of those conventionally used and is limited only by chemical-physical considerations, such as solubility and lack of reactivity with liposomes, and by the route of administration. The excipients may also at times have the effect of the improving the delivery or penetration of the liposomal formulation to a target tissue, for improving the stability of the liposomal formulation, for slowing clearance rates, for imparting slow release properties, for reducing undesired side effects etc. The excipient may also be a substance that stabilizes the formulation (e. g. a preservative), for providing the formulation with an edible flavor, etc. The excipient may include additives, colorants, diluents, buffering agents, disintegrating agents, moistening agents, preservatives, flavoring agents, and pharmacologically compatible carriers. As an example, when treating a neurodegenerative condition, the excipient may be a molecule which is known to promote or facilitate entry through the blood brain barrier (BBB) such as transferin receptor-binding agents, antibodies, or any drug that by itself transfers through the BBB.

The pharmaceutical composition of the invention may have an advantage for the treatment of a variety of conditions typically those are the conditions which are known to be treated (in at lease a phase of their course by the administration of GC. Examples of such conditions include neurodegenerative conditions and cancer, as detailed hereinafter. To this end, the liposomal formulation of the invention may comprise one or more active ingredients, in addition to the GC or GC derivative. The additional active ingredients may be in a free form or also encapsulated in liposomes (together or separated from the liposomes containing the GC derivative). For example, when treating cancer, the additional active ingredient may be a cytotoxic drug, such as doxorubicin, encapsulated in the same or different liposomes. For treating a neurodegenerative condition, the liposomal formulation may be combined with Copaxone or Betaferone.

The following is a non-limiting list of medical conditions which may be treated or prevented with the liposomal formulation of the invention additional conditions, which are known to benefit from GC treatment, are also included in the scope of the invention:

Endocrine Disorders including primary or secondary adrenocortical insufficiency; Congenital adrenal hyperplasia Hypercalcemia associated with cancer, nonsuppurative thyroiditis.

Collagen Diseases including, for example, during an exacerbation or as maintenance therapy in selected cases of Dermatologic Diseases including, for example, Pemphigus Bullous dermatitis, Severe erythema multi-herpetiformis forme (Stevens-Severe seborrheic Johnson syndrome) dermatitis Exfoliative dermatitis Severe psoriasis Mycosis fungoides.

Allergic States including, for example, control of severe or incapacitating allergic conditions unresponsive to adequate trials of conventional treatment in: Bronchial asthma, Drug hypersensitivity Contact dermatitis reactions, Atopic dermatitis, Urticarial transfusion, Serum sickness reactions, Seasonal or perennial, Acute noninfectious allergic rhinitis laryngeal edema.

Ophthalmic Diseases including, for example, severe acute and chronic allergic and inflammatory processes involving the eye, such as: Herpes zoster ophthalmicus, Sympathetic ophthalmia Iritis, iridocyclitis Anterior segment Choriorentinitis inflammation Diffuse posterior uveitis, Allergic conjunctivitis and choroiditis, Allergic corneal margina,1 Optic neuritis ulcers, Keratitis.

Respiratory Diseases including, for example, symptomatic sarcoidosis Loeffler's syndrome not Berylliosis manageable by other Fulminating or disseminate, not manageable by other means, Aspiration pneumonitis, tuberculosis optionally used concurrently with appropriate antituberculous chemotherapy.

Hematologic Disorders, including acquired (autoimmune) hemolytic anemia, Idiopathic thrombocytopenic purpura, secondary thrombocytopenia, Erythroblastopenia (RBC anemia). Congenital (erythroid) hypoplastic anemia.

Neoplastic Diseases, including, for example, for management of: Leukemias and lymphomas, myeloma, breast cancer and prostate cancer.

Edematous States including, for example, to induce diuresis or remission of proteinuria in the nephrotic syndrome, without uremia, of the idiopathic type or that due to lupus erythematosus.

Nervous System, including, for example, acute exacerbations of multiple sclerosis (MS).

As well as other conditions, such as tuberculous meningitis with sub-arachnoid block or impending block when used concurrently with appropriate antituberculous chemotherapy; Trichinosis with neurological or myocardial involvement.

Thus, the invention also pertains to a method of treatment or prevention of a disease or pathological condition, the method comprises providing a subject in need of said treatment an amount of the liposomal formulation of the invention, the amount being effective (hereinafter the "effective amount") to treat or prevent the disease or pathological condition. Preferred conditions to be treated by the present invention are cancer and neurodegenerative conditions.

The term "treatment" as used herein denotes the administering of a an amount of the GC or GC derivative encapsulated in a liposome effective to ameliorate undesired symptoms associated with a disease, to prevent the manifestation of such symptoms before they occur, to slow down the progression of the disease, slow down the deterioration of symptoms associated with the disease, to enhance an onset of a remission period of a disease, to slow down any irreversible damage caused in a progressive chronic stage of a disease, to delay the onset of said progressive stage, to lessen the severity or cure a disease, to improve survival rate or more rapid recovery from a disease, to prevent a disease form occurring, or a combination of two or more of the above.

As an example, when referring to neurodegenerative conditions, treatment denotes inhibition or slowing down of abnormal deterioration of the nervous system as well as prevention in subjects with high disposition of developing a neurodegenerative condition (as determined by considerations known to those versed in medicine) or for preventing the re-occurrence of an acute stage of a neurodegenerative condition in a chronically ill subjects. In the latter case, the pharmaceutical composition comprising the liposomal GC derivative may be administered to a subject who does not have a neurodegenerative condition but is at high-risk of developing such a condition, e.g. as a result of exposure to an agent which is known to cause abnormal generation of reactive oxidative species or subjects with family history of the disease (i.e. genetic disposition).

Further, as an example, when the disease is cancer, treatment denotes, inter alia, inhibition or reduction of the growth and proliferation of tumor cells: including arresting growth of the primary tumor, or decreasing the rate of cancer related mortality, or delaying cancer related mortality, which may result in the reduction of tumor size or total elimination thereof from the individual's body, or decreasing the rate of occurrence of metastatic tumors, or decreasing the number of metastatic tumors appearing in an individual.

The liposomal GC derivative may be provided as a single dose, however is preferably administered to a subject in need of treatment over an extended period or time (e.g. to produce a cumulative effective amount) in a single daily dose, in several doses a day, as a single dose for several days, etc. The treatment regimen and the specific formulation to be administered will depend on the type of disease to be treated and may be determined by various considerations, known to those skilled in the art of medicine, e. g. the physicians.

The term "effective amount" or "therapeutically effective amount" is used herein to denote the amount of the GC derivative when loaded in the liposome in a given therapeutic regimen which is sufficient to achieve a desired effect, e.g. inhibition or reduction of the growth and proliferation of tumor cells, or inhibition or reduction of degradation of nerve cells and thereby the deterioration of the nervous system. The amount is determined by such considerations as may be known in the art and depends on the type and severity of the condition to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the mode of administration, type of vehicle carrying the amphipathic weak acid/base, the reactivity of the GC derivative, the liposome's distribution profile within the body, a variety of pharmacological parameters such as half life in the body after being released from the liposome, on undesired side effects, if any, on factors such as age and gender of the treated subject, etc.

The term "administering" is used to denote the contacting or dispensing, delivering or applying the liposomal formulation, to a subject by any suitable route for delivery thereof to the desired location in the subject, these include oral, parenteral (including subcutaneous, intramuscular and intravenous, intraarterial, intraperitoneally) and intranasal administration as well as by as well as intrathecal and infusion techniques.

According to one embodiment, the formulations used in accordance with the invention are in a form suitable for injection. The requirements for effective pharmaceutical vehicles for injectable formulations are well known to those of ordinary skill in the art [See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986)].

It is noted that humans are treated generally longer than experimental animals as exemplified herein, which treatment has a length proportional to the length of the disease process and active agent effectiveness. The doses may be a single dose or multiple doses given over a period of several days.

While the following disclosure provides experimental data with animal model, there are a variety of acceptable approaches for converting doses from animal models to humans. For example, calculation of approximate body surface area (BSA) approach makes use of a simple allometric relationship based on body weight (BW) such that BSA is equal to body weight (BW) to the 0.67 power [Freireich E. J. et. al. Cancer Chemother. Reports 1966, 50(4) 219-244; and as analyzed in Dosage Regimen Design for Pharmaceutical Studies Conducted in Animals, by Mordenti, J, in J. Pharm. Sci., 75:852-57, 1986]. Further, allometry and tables of BSA data have been established [Extrapolation of Toxicological and Pharmacological Data from Animals to Humans, by Chappell W & Mordenti J, Advances in Drug Research, Vol. 20, 1-116, 1991 (published by Academic Press Ltd)]

Another approach for converting doses is a pharmacokinetic-based approach using the area under the concentration time curve (AUC) or Physiologically Based PharmacoKinetic (PBPK) methods are described [Voisin E. M. et al. Regul Toxicol Pharmacol. 12(2):107-116. (1990)].

The invention will now be described by way of non-limiting examples showing the effect of SSL-MPS on EAE and lymphoma cells.

DESCRIPTION OF SPECIFIC EXAMPLES

General
Materials

Hydrogenated soybean phosphatidylcholine (HSPC) was obtained from Lipoid KG (Ludwigshafen, Germany).

N-carbamyl-poly-(ethylene glycol methyl ether)-1,2-distearoyl-sn-glycero-3-phosphoethanolamine triethyl ammonium salt (PEG-DSPE) (the polyethylene moiety of this phospholipid having a molecular mass of 2000 Da) was obtained from Genzyme Liestale, Switzerland.

Cholesterol (>99% pure) was obtained from Sigma (St. Louis, Mo., USA).

[$^3$H] Cholesteryl hexadecyl ether (45 Ci per mmol) was from NEN Life Science Products (Boston, Mass., USA). tert-Butanol (99% pure) was purchased from BDH, Poole, UK.

The weak acid steroids, the pro-drugs methylprednisolone sodium hemisuccinate (MPS) and hydrocortisone sodium hemisuccinate (HYD), were obtained from Pfeizer, Belgium All the other chemicals, including buffers were of analytical grade or better, and were obtained from Sigma. Purified water was obtained from WaterPro PS HPLC/Ultrafilter Hybrid model, (Labconco, Kansas City, Mo., USA).

Methods
Liposome Preparation

A stock solution HSPC/Cholesterol/PEG-DSPE-2000 at molar ratio of 55:40:5 was dissolved in ethanol at 70° C. to a final gel lipid concentration of 62.5% (w/v). The solution was then incubated at 70° C. until all the lipids are dissolved to a clear solution. The stock solution was then added to a solution of calcium acetate 200 mM at 70° C. to receive 10% lipid concentration (w/v) hence reaching a final ethanol concentration of 16% (w/v). The mixture was constantly stirred at 70° C. to receive a milky dispersion at this stage lipids were hydrated to form multi lamellar liposome (MLV) dispersion.

The vesicles that were formed were downsized using extrusion through a polycarbonate filter of defined pore size starting with 400-nm and ending with 50-nm pore size filters, as the last extrusion step under low to medium pressure. This processes results in 80±15-nm liposomes. The extrusion device (Northern Lipids, Canada) was kept in a constant temperature of 70° C. during the entire procedure.

The removal of extraliposomal Ca acetate to create the Ca acetate gradient {[Ca acetate] in liposome>>[Ca acetate] in medium} was created by dialysis against dextrose 5% or saline 0.9 at 4° C. (4 exchanges×100 volume each, the final one over night).

Liposome phospholipids concentration was determined from organic phosphorus concentration by a modified Bartlet procedure [Shmeeda, H., et al. In: Methods in Enzymology "Liposomes", (Düzgünes, N., ed.), 367:272-292 (2003)]. Lipid concentration in the resulting liposome stock solution was 40 mM.

The amount of calcium inside the liposomes was determined by the use of atomic absorption spectrometry (AAS).
Preparation and Characterization of Radioactive-SSL

[$^3$H] cholesteryl ether-labeled sterically stabilized liposomes (SSL) composed of HSPC:Chol:$^{2000}$PEG-DSPE (55:40:5 mole ratio), and a trace amount of [$^3$H] cholesteryl hexadecyl ether (0.125 µCi/µmol PL) were prepared as described above. The liposome size was determined by Dynamic Light Scattering (DLS) to be 87±15 nm.
Loading of GC derivative Into Liposomes A stock solution of methylprednisolone hemi succinate sodium salt (MPS, the GC derivative) was dissolved in 5% dextrose (pH 7.2) to a concentration of ~9 mg/ml and added to the preformed SSL dispersion after the calcium acetate gradient was established. MPS concentration was ~9 mg/ml and phospholipid ~32 mM phosphate.

Loading was achieved by incubation of the components above for the desired time at 62° C. (above matrix lipid $T_m$). Liposomes were then cooled to 4° C. and dialyzed against 5% dextrose at 4° C. to remove acetate released during loading and to remove unloaded drug or alternatively unloaded drug was removed by the ion exchanger Dowex 1×400 mesh (Cl$^-$ form).
State of Aggregation, Partition Coefficient and Surface Tension of MPS
1. State of Aggregation of MPS Aggregation of MPS was determined from the change in turbidity measured as intensity of light scattered at 90° to excitation beam using a spectrofluormeter under conditions that MPS lack absorbance (excitation and emission at the same wavelength Ex=600 nm Em=600 nm). There is a large increase in the light scattered by MPS solution/dispersion due to formation of aggregates.

The intensity of scattered light (at 90° to the excitation), also defined as turbidity is proportional to concentration and to the size of the aggregates. [Zuidam, N. J. and Barenholz, Y., *Biochim. Biophys. Acta* 1368:115-128 (1998)]. The state of aggregation of MPS was tested in the following manner: To quartz cuvette MPS (2 ml) at concentration of ~6.5 mg/ml MPS was added. The solution was tittered with HCl (1.756M) and light scattering using excitation and emission at (both at 600 nm with attenuation of 1%) and pH of the solution was monitored.

2. Partition Coefficient

Partition coefficient (logD) of some GC derivatives (which are amphipathic weak acids) was determined by the 'shake flask' as described [Samuni, A. M. and Barenholz, Y., *Free Radicals Biol. Med.* 22:1165-1174 (1997)].

3. Surface Tension

Surface tension was measured using µtrouge S (Kibron Inc., Helsinki Finland). A solution containing GC derivative (300 µL) was placed in the well after calibration and zeroing of the sensor using pure water and air. The measurement was performed at 26° C.

Precipitation of MPS Inside SSL

MPS precipitation inside the intraliposomal aqueous phase of the vesicle was visualized using Cryo TEM as described [Lasic, D. D., Frederik, P. M., Stuart, M. C. A., Barenholz, Y. and McIntosh, T. J., Gelation of liposome interior. A novel method for drug encapsulation. *FEBS Lett.* 312, 255-258 (1992); Lasic, D. D., et al. *Biochim. Biophys. Acta* 1239, 145-156 (1995)].

Precipitation Studies

To 600 mOsm Ca-acetate solution at 63° C. and at different pH points MPS was added at final concentration of 5 mg/ml, then mixed solution was incubated for 40 minutes after which the solution was centrifuged and the supernatant was analyzed using HPLC.

Loading Efficiency

Loading efficiency is the ratio between MPS/phospholipid concentrations after and before loading. The quantification of MPS was done in an HPLC apparatus as described by Anderson, and Taphouse 1981 [Anderson B. D. and Taphouse. V. J Pharm Sci, 70:181-6 (1981)] quantification of phospholipid was done by modified Bartlet procedure [Shmeeda, H., et al. In: Methods in Enzymology "Liposomes", (Düzgünes, N., ed.), 367:272-292 (2003)].

Stability Determination

Determination of MPS Release from Liposome

The level of MPS released from SSL-MPS was determined by first separating the liposomes from free MPS using gel exclusion chromatography on Sepharose cross-linked CL-4B column using. Liposomes were eluted at the void volume and the free MPS at the later eluted fractions (FIG. 3A-3B).

Stability upon storage at 4° C. and kinetic of release at 37° C. in 80% plasma was determined by gel exclusion chromatography described above. Then the different column fractions were analyzed as described above, for MPS, phospholipids and Ca in the void volume fraction.

In addition, SSL-MPS were incubated with 80% human inflamed synovial fluid at a ratio of 80% plasma at 37° C. Then at different time points sample were vortexed with the anion exchange resin, DOWEX 1×400 mesh (Cl⁻ form), which bind only free MPS. The samples were analyzed for liposome encapsulated MPS and liposome phospholipid content.

Results

Table 1 below provides logD and pKa of the tested GC derivatives, as calculated using Advanced Chemistry Development (ACD/Labs) [Software Solaris V4.67 (1994-2005 ACD/Labs) SciFinder SCHOLAR Version 2004.2 © American Chemical Society 2004].

TABLE 1 logD and pKa of different GC derivatives

| Modified GC | logD at pH 7 | pKa |
|---|---|---|
| Prednisolone phosphate | −4.25 | 1.67 ± 0.10 |
| Prednisolone hemisuccinate | −0.64 | 4.29 ± 0.17 |
| Methylprednisolone phosphate | −3.76 | 1.67 ± 0.10 |
| Methylprednisolone hemisuccinate | −0.15 | 4.29 ± 0.17 |
| Dexamethasone phosphate | −3.88 | 1.67 ± 0.10 |
| Dexamethasone hemisuccinate | −0.27 | 4.29 ± 0.17 |

Turbidity, Partition Coefficient and Surface Tension of MPS

The turbidity (indicating the aggregation) of MPS was determined. The results shown in FIG. 1A indicate that at pH 7.2 the amphipathic weak acid derivative (the pro-drug) is non-aggregated water soluble and in acidic pH, it aggregates, therefore showing increase in turbidity. The decline in turbidity observed at very low pH, was due to the formation of very large aggregates which precipitated. The doted arrow indicates the point of transition from titration with HCl (µmol of H⁺, left side of arrow) to titration with NaOH (µmol of OH⁻, right side of arrow).

Figure 1B:
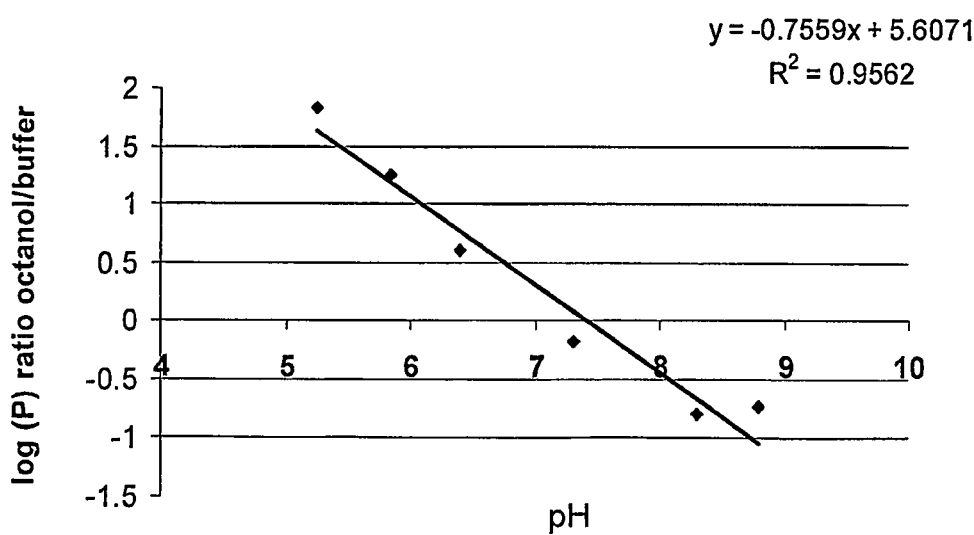
Figure 1C:
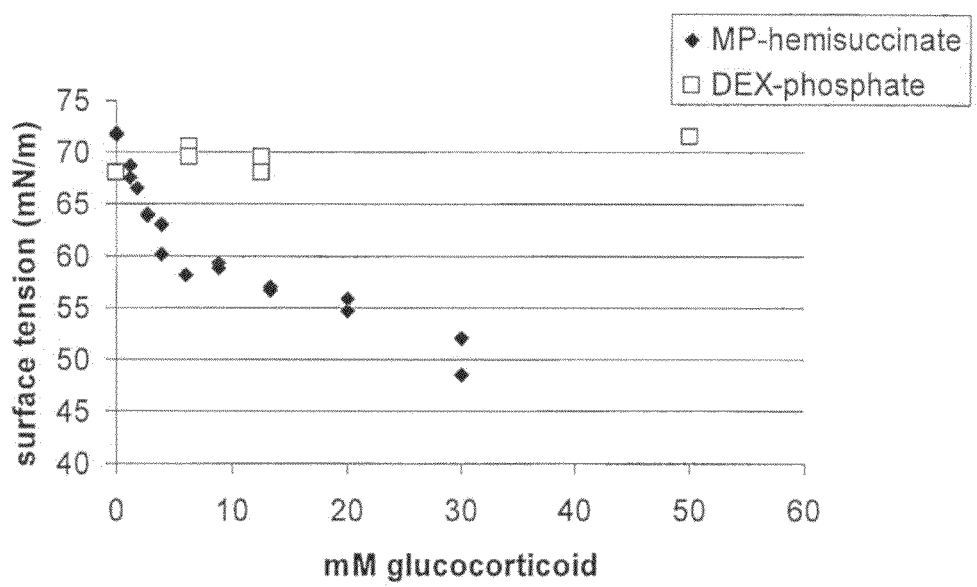

Partition coefficient of MPS was determined at different pH points. As shown in FIG. 1B, MPS is indeed an amphipathic substance.

Further, the surface tension of MPS was determined and as evident from FIG. 3C, MPS is surface active at all concentrations used (0.785-30 mM) and has a CAC (critical association/aggregation concentration) point at ~5 mM while GC that has a phosphate group (a strong acidic group) such as dexamethasone phosphate was not surface active at least up to concentration of 50 mM and did not self associate to form micelles and/or other organized assemblies.

Precipitation of MPS by Calcium Ion

The precipitation of MPS in the presence of calcium acetate solution was determined as described above. Table 2 shows the percent of MPS that precipitated in the presence of calcium ions, i.e. at different pH. As shown, precipitation already occurred at pH 6.8. Precipitation was increased to a very large extent (97% of the MPS) at pH around the pKa of GC (pH 4.5).

TABLE 2 precipitation of MPS

| pH | % MPS precipitated |
|---|---|
| 6.8 | 44.1 |
| 6.2 | 42.8 |
| 4.5 | 96.6 |

General Loading Efficiency for Different Liposomal Formulations

1. Liposome Loading Efficiency

Three separate batches (identified by dates) were used in order to determine loading efficacy of the drug into the liposomes (HSPC:Chol:$^{2000}$PEG-DSPE (55:40:5 mole ratio), as summarized in Table 3.

TABLE 3

Loading efficiency into SSL

| | mg/ml MPS | mM phosphate | MPS/lipid (mg/μmole) | % Encapsulation |
|---|---|---|---|---|
| 18JUL04 | | | | |
| Before dialysis[a] | 7.46 | 39.80 | 0.188 | |
| After dialysis[b] | 7.56 | 40.70 | 0.186 | 99.1 |
| 06APR05 | | | | |
| Before dialysis[a] | 6.22 | 33.20 | 0.19 | |
| After dialysis[b] | 4.99 | 27.60 | 0.18 | 96.6 |
| 04MAY05 | | | | |
| Before dialysis[a] | 9.68 | 45.73 | 0.21 | |
| After dialysis[b] | 6.35 | 32.19 | 0.20 | 93.2 |

[a]MPS in liposome + MPS in the extraliposome medium
[b]MPS in liposome only

2. Loading Efficiency of MPS for Different Liposomal Formulations

It was determined that the optimum conditions for efficient loading include ~600 mOsm of Calcium acetate. The loading efficiency of MPS in HSPC:Chol:$^{2000}$PEG-DSPE (55:40:5 mole ratio) liposomes with this MPS/phospholipids ratio was obtained when using initial pro-drug concentration between 5-10 mg/ml, preferably 9 mg/ml. The concentration of the pro-drug in the final formulation was ~6.5 mg/ml which was used in the following experiments (hereinafter termed the SSL-MPS formulation or in brief SSL-MPS).

Figure 2A:
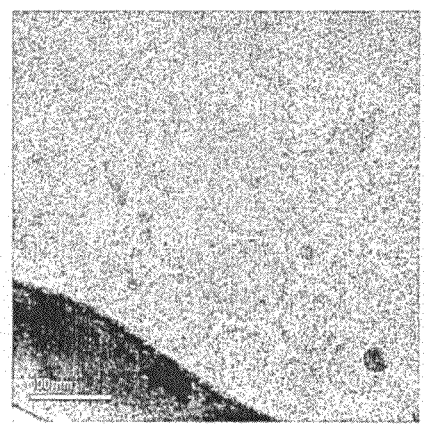
FIGS. 2A-2B—are Cryo-TEM (transmission elecron microscopy) images of liposomes before (FIG. 2A) and after (FIG. 2B) active loading of MPS.
Figure 2B:
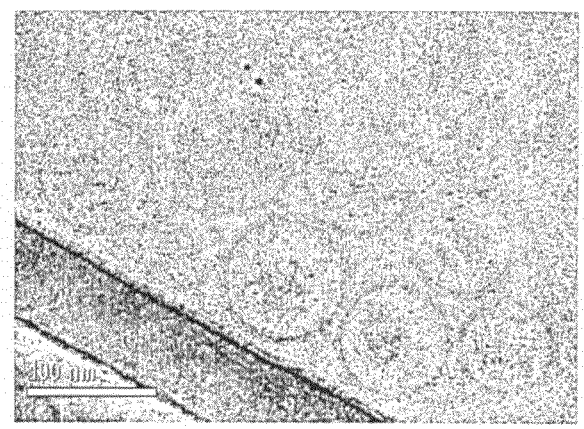

FIG. 2A-2B are Cryo-TEM images of liposomes before (FIG. 2A) and after (FIG. 2B) loading clearly showing location of the precipitate in the internal aqueous space of the liposome.

Stability of Liposomal Formulation

The concentration of MPS in SSL-MPS (i.e. intact liposomal formulation) over 14 months was determined as described above. FIG. 3A shows that after 14 months ~80% of MPS was retained in the liposome. Part of the free MPS was hydrolyzed to its active form, methylrednisolone (MP). FIG. 3B provides a Sepharose 4B size-exclusion chromatograph of the liposomal preparation at after 14 months of storage at 4° C., with an enlargement (FIG. 3C) of the graph at fractions 8 to 17, showing the existence of free MPS as well as free MP.

Figure 4:
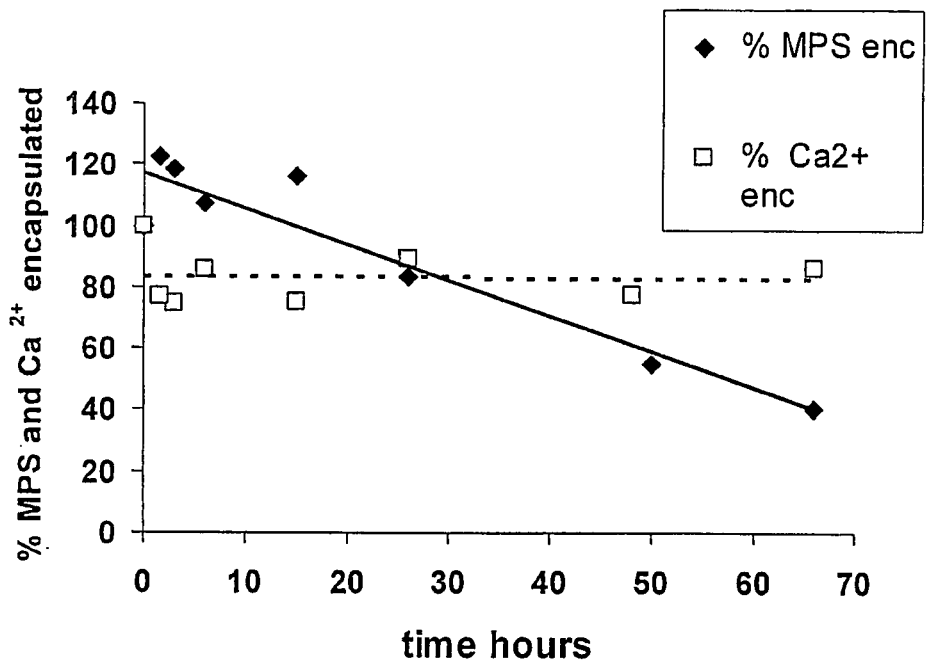
FIG. 4 is a release profile of MPS and $Ca^{2+}$ from SSL-MPS when incubated in plasma.

Further, stability of SSL-MPS in clinical relevant milieus was determined. FIG. 4 shows the stability of the liposomal formulation in human plasma. The retention of 100% of the encapsulated calcium in the encapsulated liposome under condition that MPS is released (with a half life in liposome of 50 hours) indicates that the liposomes are intact for at least 66 hours in plasma. This suggests that the release of MPS is due to its amphiphacy. The half life of MPS release is in a similar value to SSL half life in plasma post i.v. injection.

Example 1

Multiple Sclerosis (MS)

Induction of Acute EAE Experimental Animal Model using Proteolipid Protein (PLP)

6-7 week old SJL female mice were immunized by subcutaneous injection with an emulsion containing proteolipid protein (PLP) 139-151 peptide and complete Freund's adjuvant (CFA), containing 150 ug of peptide and 200 ug of *Mycobacterium tuberculosis*. In order to boost the immune system Pertussis Toxin (PT) 150 ng were injected intraperitoneally (i.p.) to the mice on the first day and 48 hours later.

Each mouse was examined daily for clinical signs of EAE using the following Table 4:

TABLE 4 clinical signs scoring

| Score | Signs | Description |
|---|---|---|
| 0 | Normal behavior | No neurological signs |
| 1 | Distal limp tail | The distal part of the tail is limp and droops |
| 1.5 | Complete limp tail | The whole tail is loose and droops |
| 2 | Complete limp tail with righting reflex | The whole tail is loose and droops. Animal has difficulties to return on his feet when it is laid on his back |
| 3 | Ataxia | Woobly walk- when the mouse walks the hind legs are unsteady |
| 4 | Early paralysis | The mouse has difficulties standing on its hind legs but still has remnants of movement |
| 5 | Full paralysis | The mouse can't move its legs at all, it looks thinner and emaciated. Incontinence |
| 6 | Moribund/death | |

The number of mice in each animal group which developed the disease (sick) was summed and the percentage thereof was calculated.

In addition, the mean maximal score (MMS) by summing the maximal scores of each of the 10 mice in the group and calculating therefrom the mean maximal score of group according to the following equation:

Σmaximal score of each mouse/number of mice in the group

Further, the mean duration of disease (MDD) expressed in days was calculated according to the following equation:

Σduration of disease of each mouse/number of mice in the group

Further, each group's mean score (GMS) (burden of disease) was determined by summing the scores of each of the 10 mice in the group and calculating the mean score per day, according to the following equation:

Σtotal score of each mouse per day/number of mice in the group.

Treatment of EAE with SSL-MPS

The EAE induced mice were divided into treatment groups according to the following Table 5.

TABLE 5 treatment design

| Treatment | No. mice/ group | Day of injection | No. of injection |
|---|---|---|---|
| Control | 8 | 0 | 0 |
| Free-MPS 50 mg/kg BW | 9 | 14 | 1 |
| SSL-MPS 50 mg/kg BW | 9 | 14 | 1 |

Figure 5:
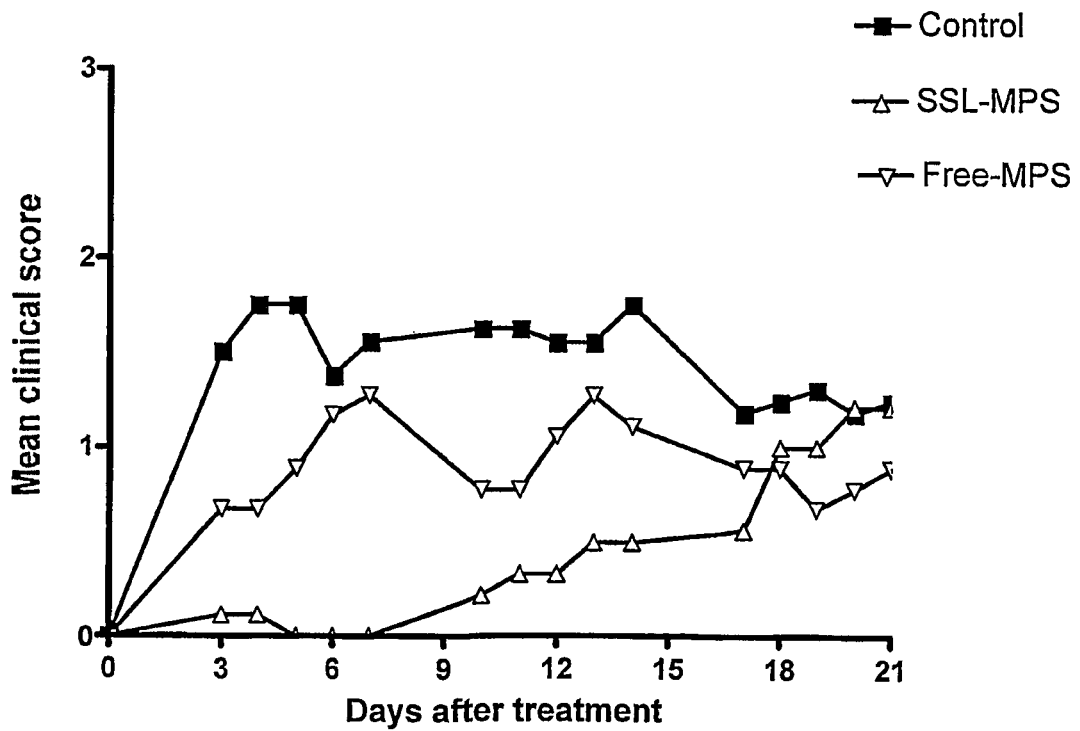
FIG. 5 is a graph showing the effect of SSL-MPS treatment in Experimental Autoimmune Encephalomyelitis (EAE).

Follow up was conducted for a period of 3 weeks, and clinical signs of EAE were determined at different time points. For each group, the incidence, MMS=mean maximal score; MDD=mean disease duration (days); MDO=mean day of onset and mean score were determined (Table 6). Further, for each group the mean clinical scores at each time point was determined (FIG. 5).

TABLE 6 observed clinical signs

| Group | Incidence | MMS | MDO | MDD | Mean Score |
|---|---|---|---|---|---|
| Control | 6/8 | 3 ± 0.365 | 13.7 ± 0.667 | 18.5 ± 0.5 | 1.4 ± 0.104 |
| SSL-MPS | 5/9 | 2.2 ± 0.583 | 20.4 ± 2.16 | 6 ± 2.07 | 0.444 ± 0.090 |
| Free-MPS | 7/9 | 2.35 ± 0.39 | 16.7 ± 1.83 | 10.9 ± 2.7 | 0.861 ± 0.105 |

Treatment of Severe Disease Burden

Figure 6A:
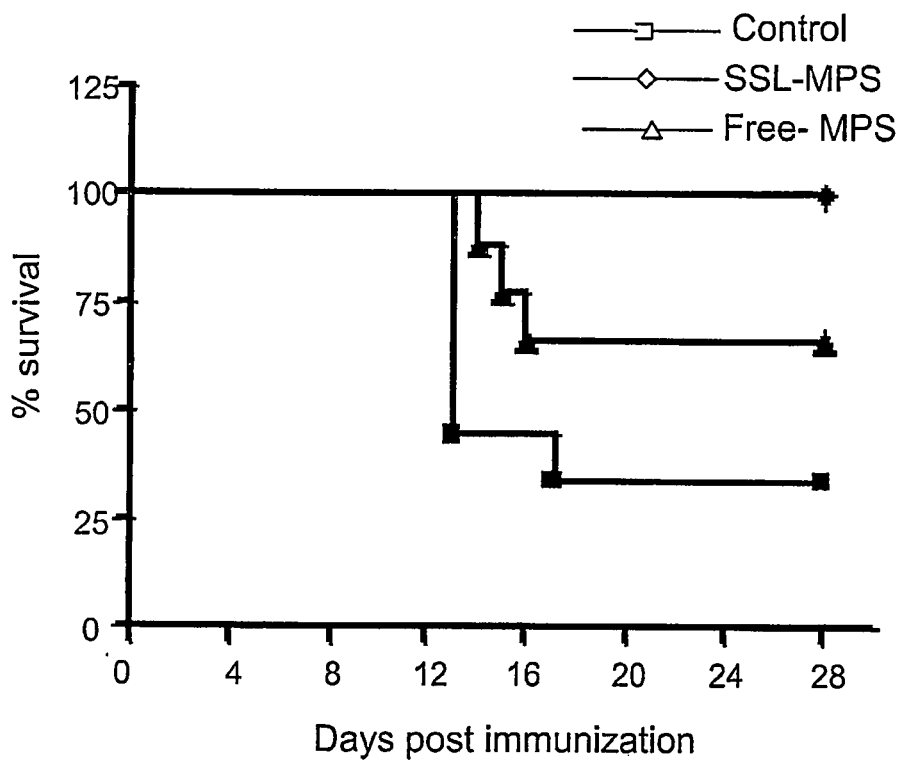
FIG. 6A-6B are graphs showing the effect of SSL-MPS treatment on survival rate (%) (FIG. 6A) and on mean clinical score (FIG. 6B) in EAE induced animals.

For mice showing a severe disease burden (determined by summing the scores of each of the 10 mice in the group and calculating the mean score per day, according to the following equation: Σtotal score of each mouse per day/number of mice in the group) a different treatment was applied. Specifically, after immunization as described above, mice were treated with 50 mg/kg BW SSL-MPS (days 10, 14, 18) or with free-MPS 50 mg/kg BW (days 10, 14, 18) or dextrose 5% (days 10, 14, 18). For each group, the incidence, MMS=mean maximal score; MDD=mean disease duration (days); MDO=mean day of onset and mean score were determined Table 7. Further, for each group the mean clinical scores at each time point was determined (FIG. 6B) as well as the survival curve (FIG. 6A).

TABLE 7 observed clinical signs

| Group | Incidence (#dead) | MMS | MDO | MDD | Mean Score |
|---|---|---|---|---|---|
| Control | 9/9 (6) | 5.56 ± 0.24 | 11.3 ± 0.28 | 7.56 ± 2.37 | 4.18 ± 0.203 |
| SSL-MPS | 9/9 (0) | 2.61 ± 0.36 | 13.9 ± 0.92 | 6.78 ± 1.88 | 0.705 ± 0.09 |
| Free-MPS | 9/9 (3) | 4.44 ± 0.50 | 12.67 ± 0.65 | 10.11 ± 1.92 | 2.62 ± 0.208 |

The fact that 6 out of 9 died in the control group (untreated) and the high mean clinical score of the control group confirm that the disease developed was severe (as compared Table 6 showing the effect in animals which developed a mild disease, where no mice died and disease mean score of the untreated control group was less than 2.)

Figure 6B:
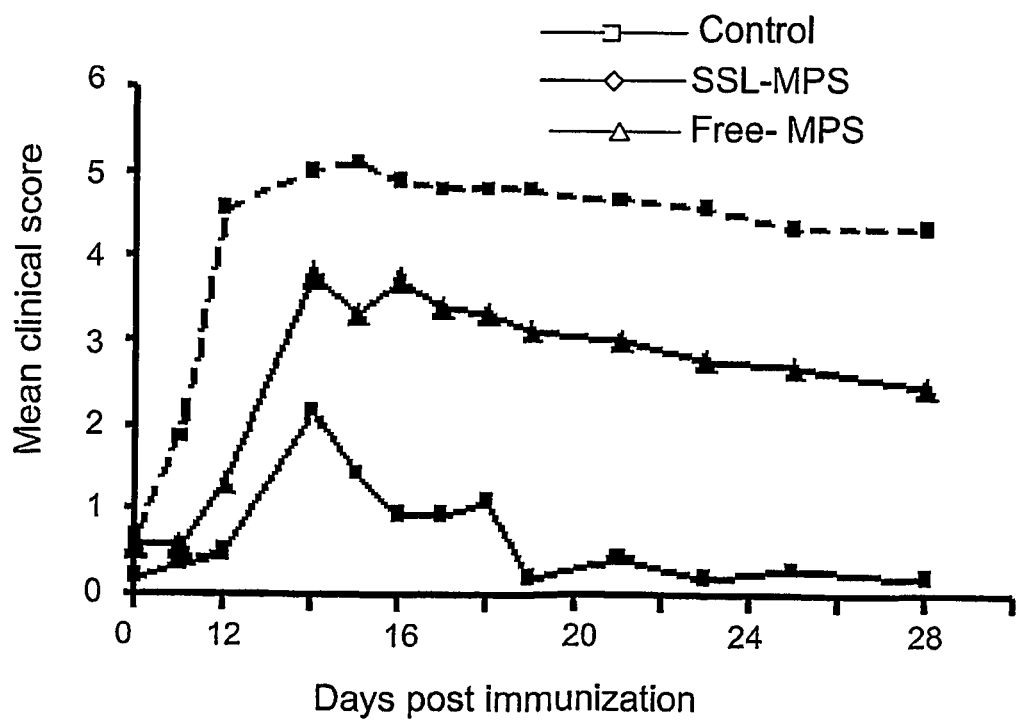

The survival curve FIG. 6A, and mean clinical score in FIG. 6B, also both show that the disease developed with a severe mean score.

Specific attention should be given to the following observations obtained with respect to the animals which developed a severe burden of disease:

1. While there was mortality in the control and free-MPS groups, all animal survived in the SSL-MPS treated group;

2. At day 19 (FIG. 6B) treatment with SSL-MPS led to a mean clinical score close to 0, as compared to that of the free-MPS treated group or control group, being ~3 and ~4.8 respectively.

3. Mean score of the disease (Table 5) for the SSL-MPS treated group was 4 times lower than that of the control and ~2 times lower than that of the free-MPS treated group.

Thus, it was concluded that SSL-MPS has a beneficial therapeutic effect during severe states of the disease as compared to free MPS.

Comparison with Conventional MS Drugs in the Acute EAE Model

SJL female mice (6-7 week old) were immunized as described above. The immunized mice were divided into groups and each group was treated on days 8, 11, and 14 post immunization with the following treatment formulations:
Group I—50 mg/kg BW SSL-MPS;
Group II—free-MPS 50 mg/kg BW;
Group III—Dextrose 5%;
Group IV—Coapxone 250 ug/0.1 cc;
Group VI—Betaferon human 2000 ui/0.1 cc.

For each group, the incidence, MMS=mean maximal score; MDD=mean disease duration (days); MDO=mean day of onset and mean score were determined Table 8. Further, for each group the mean clinical scores at each time point was determined (FIG. 7)

TABLE 8 observed clinical signs

| Group | Incidence (#dead) | MMS | MDO | MDD | Mean Score |
|---|---|---|---|---|---|
| Control | 10/10 (3) | 3.9 ± 0.526 | 11 ± 0 | 9.8 ± 1.2 | 2.3 ± 0.223 |
| Betaferone | 10/8 (3) | 3.15 ± 0.753 | 10.3 ± 1.84 | 7.7 ± 1.51 | 1.8 ± 0.245 |
| Compaxone | 10/8 (3) | 2.9 ± 0.69 | 9.9 ± 1.74 | 8.1 ± 1.72 | 1.8 ± 0.219 |
| SSL-MPS | 10/9 (1) | 2.7 ± 0.578 | 11.3 ± 1.48 | 3.5 ± 1.13 | 0.74 ± 0158 |

Figure 7:
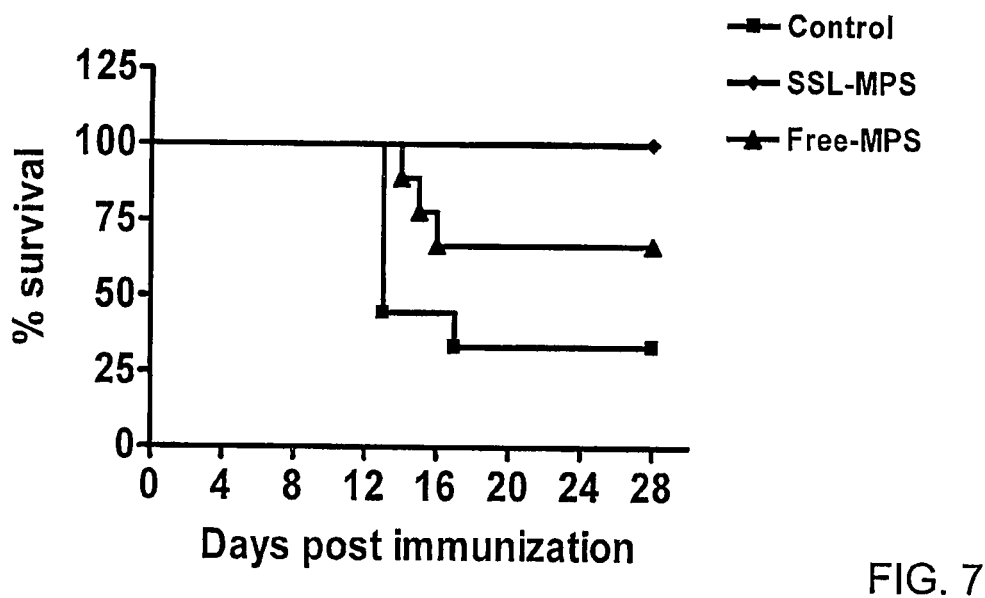
FIG. 7 is a graph showing the effect of SSL-MPS treatment on EAE compared to the effect of Betaferon and Copaxone, two conventional drugs.

FIG. 7 presents the clinical score at different time points during the follow-up period. As observed, overall effect of SSL-MPS on the mean burden of the disease was 3 time lower than that of the control of free MPS treated groups. Further, SSL-MPS was effective in lowering the mean clinical score from severe level of early paralysis to distal limp tail. Only one mouse died in the SSL-MPS treated group compared to 3 and 5 death incidence in the other groups.

Thus, it was concluded that SSL-MPS has a beneficial effect over the currently much more superior effect over currently clinically available drugs and this formulation has the ability to lower mean clinical score from severe state of early paralysis to mild one.

Induction of Acute EAE Using MOG (Myelin Oligodendrocyte Glycoprotein)

Induction of chronic EAE using MOG 35-55 peptide was performed as described [Offen D et al *J Mol Neurosci.* 15(3): 167-76 (2000)]. In general, female C57B1/6 mice were inoculated (s.c. injection in the right flank) with an encephalitogenic emulsion (MOG plus CFA enriched with MT (*mycobacterium tuberculosis*). Pertussis toxin was injected i.p (250 ng/mouse) on the day of inoculation and 48 hrs later. A boost of the MOG emulsion was injected s.c. in the right flank one week after first injection.

Figure 8:
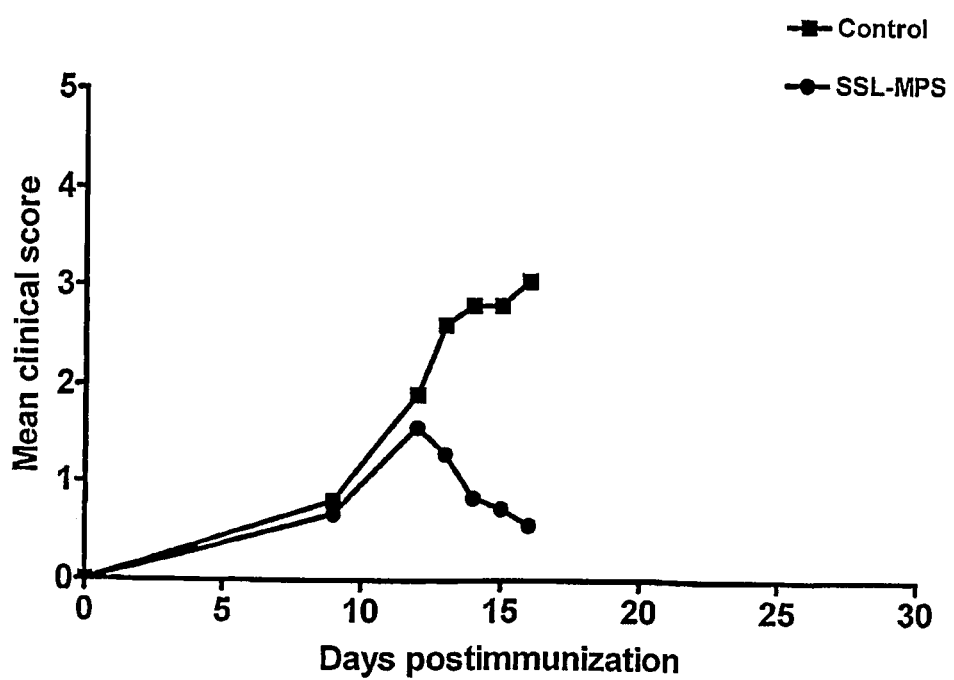
FIG. 8 is a graph showing the effect of SSL-MPS treatment in a chronic EAE animal model.

After immunization as described above, mice were treated with 50 mg/kg BW SSL-MPS (days 12, 14, 16). The mean clinical scores at each time point was determined (FIG. 8). As shown, SSL-MPS was effective in reducing the clinical signs of acute EAE.

Example 2

Cancer

Corticosteroids have proven therapeutic efficacy in a variety of cancer types and are used extensively in cancer therapy, particularly for hematological malignancies (leukemia, lymphoma, myeloma) and hormone-responsive cancers (breast and prostate carcinomas). Frequently, corticosteroids are used within the frame of treatment protocols that include chemotherapy. [Lorraine I. McKay and John A. Cidlowski. corticosteroids Cancer Medicine e.5 B.C. Decker Inc., SBN 1-55009-113-12000. by BC Decker Inc. First published 1981. Fifth Edition 2000. 01 02 0 QP 9 8 7 6 5 4 3 Printed in Canada].

At day 1 of the experiment BALB/C mice were injected i.p. with 1 million J6456 lymphoma cells (mouse T-cell lymphoma) then mice were divided into groups and treated by i.v. injections with free-MPS or SSL-MPS according to the following treatment schedule (Table 9). The median of survival as determined on Day 14 of treatment was determined and is also shown in Table 9:

TABLE 9 treatment schedule

| Group | No. of mice | Injection day | No. injection | Median survival |
|---|---|---|---|---|
| Control | 6 | 0 | 0 | 16 |
| Free-MPS 15 mg/kg BW | 10 | 5, 9, 12 | 3 | 16 |
| Free-MPS 50 mg/kg BW | 10 | 5, 9, 12 | 4 | 16 |
| SSL-MPS 15 mg/kg BW | 10 | 5, 9, 12, 16 | 4 | 19 |
| SSL-MPS 30 mg/kg BW | 10 | 5, 9, 12, 16 | 4 | 21 |

TABLE 9-continued treatment schedule

| Group | No. of mice | Injection day | No. injection | Median survival |
|---|---|---|---|---|
| SSL-MPS 50 mg/kg BW | 10 | 5, 9, 12, 16 | 4 | 23 |

The above results show that median survival time was extended by SSL-MPS-treatment in a dose-dependent manner.

In a further assay, survival of BCL-1 (mouse B cell lymphoid leukemia) tumor bearing mice was determined. According to this assay, at day 1 of the experiment BALB/C mice were injected I.P with 1 million BCL-1 lymphoma cells (B cell line, IC50 of MPS in the nmolar range). Then, the mice were divided into groups and treated at days 5, 9, 12, 16, by i.v. injections, with the following treatment formulations:

Group I—5 mg/kg BW free-MPS;
Group II—25 mg/kg BW free-MPS;
Group III—5 mg/kg BW SSL-MPS;
Group IV—50 mg/kg BW SSL-MPS.

The survival median of the different groups was determined and summarized in Table 10.

TABLE 10

Survival median

| Group | median |
|---|---|
| Control | 19 |
| Free-MPS 5 mg/kg BW | 19 |
| Free-MPS 25 mg/kg BW | 19 |
| SSL-MPS 5 mg/kg BW | 35 |
| SSL-MPS 50 mg/kg BW | 47 |

Figure 9:
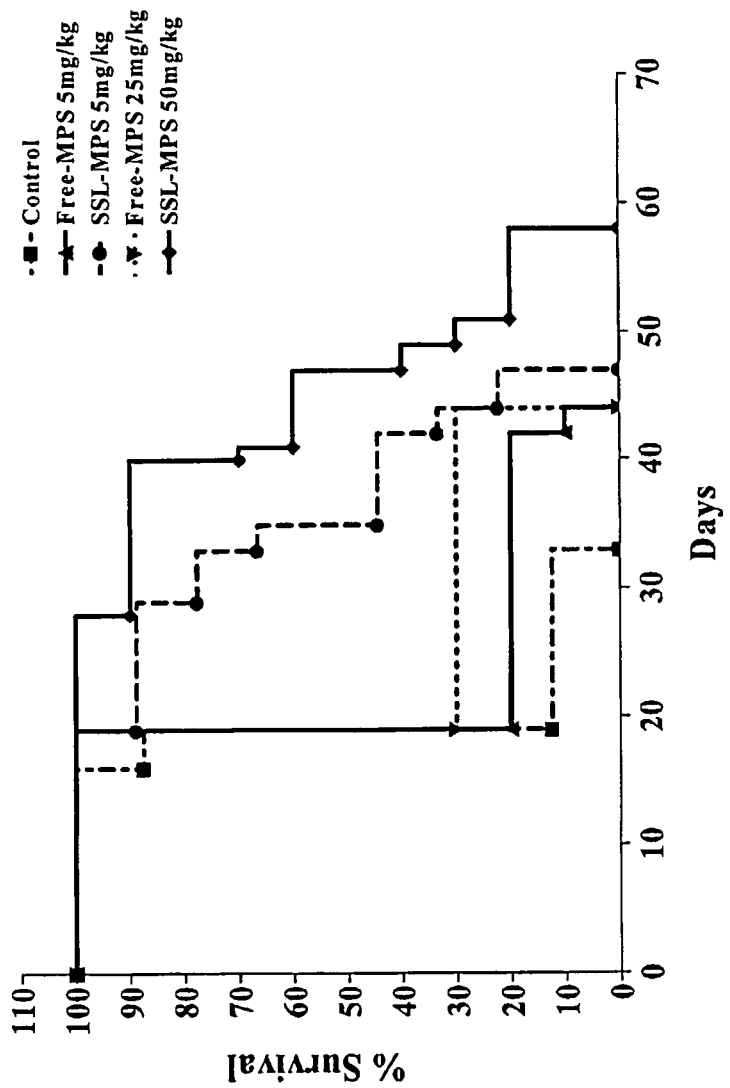
FIG. 9 is a graph showing the effect of SSL-MPS treatment on survival of BCL-1 lymphoma.

Survival curve shown in FIG. 9 exhibited a beneficial effect for SSL-MPS as compared to free MPS or the control group. It is important to note that this cell line was highly sensitive to MPS.

The invention claimed is:

1. A pharmaceutical composition, comprising:
   a liposome said liposome comprising either HSPC or DSPC in combination with cholesterol and PEG-DSPE-2000 in a molar ratio of 55:40:5, the liposome also comprising
   a glucocorticoid (GC) derivative that is an amphipathic weak base GC derivative having a pKa equal to or below 11 and a logD at pH 7 in a range of from −1.5 to 1.0 or an amphipathic weak acid GC derivative having a pKa above 3.5 and a logD at pH 7 in a range of from −1.5 to 1.0, the GC derivative being selected from the group consisting of prednisolone hemisuccinate, methylprednisolone hemisuccinate, hydrocortisone hemisuccinate, dexamethasone hemisuccinate, allopregnanolone hemisuccinate, beclomethasone 21-hemisuccinate, betamethasone 21-hemisuccinate, boldenone hemisuccinate, prednisolone 21-hemisuccinate, nandrolone hemisuccinate, 19-nortestosterone hemisuccinate, deoxycorticosterone 21-hemisuccinate, corticosterone hemisuccinate, and cortexolone hemisuccinate; and
   a counter-ion to the GC derivative
   wherein the GC derivative is retained in the liposome for at least six months.

2. The pharmaceutical composition of claim 1, wherein the GC derivative is a pro-drug which is converted to an active GC upon release thereof from the liposome into a body fluid.

3. The pharmaceutical composition of claim 1, wherein the GC derivative corresponds to an acidic GC selected from the group consisting of methylprednisolone sodium hemisuccinate (MPS), hydrocortisone sodium hemisuccinate (HYD), dexamethasone hemisuccinate and prednisolone hemisuccinate.

4. The pharmaceutical composition of claim 1, comprising a mole ratio between the GC derivative and HSPC or DSPC of between 0.01 and 2.0.

5. The pharmaceutical composition of claim 4, wherein the mole ratio is between 0.04 and 0.25.

6. The pharmaceutical composition of claim 1, for the treatment of a neurodegenerative disorder.

7. The pharmaceutical composition of claim 6, for the treatment of multiple sclerosis.

8. The pharmaceutical composition of claim 1, for the treatment of cancer.

9. A method for preparing a stable liposomal glucocorticoid (GC) derivative suitable for delivery to a target site within a body, comprising:

chemically modifying the GC to obtain a GC derivative that is an amphipathic weak base GC derivative having a pKa equal to or below 11 and a logD at pH 7 in a range of from −1.5 to 1.0 or an amphipathic weak acid GC derivative having a pKa above 3.5 and a logD at pH 7 in a range of from −1.5 to 1.0, the GC derivative being selected from the group consisting of prednisolone hemisuccinate, methylprednisolone hemisuccinate, hydrocortisone hemisuccinate, dexamethasone hemisuccinate, allopregnanolone hemisuccinate, beclomethasone 21-hemisuccinate, betamethasone 21-hemisuccinate, boldenone hemisuccinate, prednisolone 21-hemisuccinate, nandrolone hemisuccinate, 19-nortestosterone hemisuccinate, deoxycorticosterone 21-hemisuccinate, dexamethasone hemisuccinate, corticosterone hemisuccinate, and cortexolone hemisuccinate; and loading a counter-ion to the GC derivative into a liposome comprising either HSPC or DSPC in combination with cholesterol and PEG-DSPE-2000 in a molar ratio of 55:40:5; and loading the GC derivative into the liposome;

wherein the GC derivative is retained in the liposomes for at least 6 months.

10. The method of claim 9, wherein the GC of the GC derivative is a water immiscible GC.

11. The method of claim 9, wherein the GC derivative is loaded into the liposome by the formation of an ion or pH gradient across the liposome membrane.

* * * * *